United States Patent
Gorse

(10) Patent No.: US 7,881,871 B2
(45) Date of Patent: Feb. 1, 2011

(54) METHOD FOR DESIGNING SURFACES

(75) Inventor: Alain-Dominique Jean-Pierre Gorse, Mackenzie (AU)

(73) Assignee: Bio-Layer Pty Limited, Eight Mile Plains, Queensland (AU)

( * ) Notice: Subject to any disclaimer, the term of this patent is extended or adjusted under 35 U.S.C. 154(b) by 874 days.

(21) Appl. No.: 10/582,423

(22) PCT Filed: Dec. 10, 2004

(86) PCT No.: PCT/AU2004/001747

§ 371 (c)(1), (2), (4) Date: Sep. 22, 2006

(87) PCT Pub. No.: WO2005/057462

PCT Pub. Date: Jun. 23, 2005

(65) Prior Publication Data

US 2007/0099235 A1 May 3, 2007

Related U.S. Application Data

(60) Provisional application No. 60/529,605, filed on Dec. 12, 2003.

(51) Int. Cl.
*G06F 19/00* (2006.01)
*G06F 7/60* (2006.01)
*G01N 33/53* (2006.01)
*A61K 39/00* (2006.01)

(52) U.S. Cl. .......................... 702/19; 703/11; 435/7.1; 424/179.1

(58) Field of Classification Search .................. None
See application file for complete search history.

(56) References Cited

U.S. PATENT DOCUMENTS

| | | | |
|---|---|---|---|
| 3,286,009 A | 11/1966 | Yumoto et al. |
| 3,849,172 A | 11/1974 | Chin et al. |
| 4,205,952 A | 6/1980 | Cais |
| 4,267,202 A | 5/1981 | Nakayama et al. |
| 4,799,931 A | 1/1989 | Lindstrom |
| 4,985,468 A | 1/1991 | Elmes et al. |
| 5,047,445 A | 9/1991 | Nishizawa |
| 5,080,924 A | 1/1992 | Kamel et al. |
| 5,130,343 A | 7/1992 | Frechet et al. |
| 5,139,817 A | 8/1992 | Abe et al. |
| 5,238,613 A | 8/1993 | Anderson |
| 5,244,799 A | 9/1993 | Anderson |
| 5,364,907 A | 11/1994 | Rolando et al. |
| 5,384,265 A | 1/1995 | Kidwell et al. |
| 5,451,453 A | 9/1995 | Gagnon et al. |
| 5,583,211 A | 12/1996 | Coassin et al. |
| 5,683,800 A | 11/1997 | Stringfield et al. |
| 5,691,431 A | 11/1997 | Chen et al. |
| 5,789,487 A | 8/1998 | Matyjaszewski et al. |
| 5,807,937 A | 9/1998 | Matyjaszewski et al. |
| 5,832,102 A | 11/1998 | Uchida |
| 5,886,104 A | 3/1999 | Pedersen et al. |
| 5,922,161 A | 7/1999 | Wu et al. |
| 5,922,545 A | 7/1999 | Mattheakis et al. |
| 5,932,102 A | 8/1999 | Wyllie et al. |
| 5,976,813 A | 11/1999 | Beutel et al. |
| 6,001,894 A | 12/1999 | Ottersbach et al. |
| 6,013,170 A | 1/2000 | Meade |
| 6,060,530 A | 5/2000 | Chaouk et al. |
| 6,110,369 A | 8/2000 | Ditter et al. |
| 6,150,459 A | 11/2000 | Mayes et al. |
| 6,225,368 B1 | 5/2001 | D'Agostino et al. |
| 6,226,603 B1 | 5/2001 | Freire et al. |
| 6,310,149 B1 | 10/2001 | Haddleton |
| 6,329,209 B1 | 12/2001 | Wagner et al. |
| 6,346,413 B1 | 2/2002 | Fodor et al. |
| 6,403,368 B1 | 6/2002 | Jan et al. |
| 6,515,039 B1 | 2/2003 | Ulbricht et al. |
| 6,582,754 B1 | 6/2003 | Pasic et al. |
| 6,706,320 B2 | 3/2004 | Filippou et al. |
| 2002/0025380 A1 | 2/2002 | Vanmaele et al. |
| 2003/0003223 A1 | 1/2003 | Morse et al. |
| 2003/0215877 A1 | 11/2003 | Love et al. |
| 2004/0112832 A1 | 6/2004 | Sundberg et al. |

FOREIGN PATENT DOCUMENTS

| | | |
|---|---|---|
| CA | 2052783 | 4/1992 |
| CA | 2341387 | 3/2000 |

(Continued)

OTHER PUBLICATIONS

Lyne Structure-based virtual screening: an overview Drug Discovery Today vol. 7, pp. 1047-1055 (2002).*

(Continued)

*Primary Examiner*—John S Brusca
(74) *Attorney, Agent, or Firm*—Howrey LLP

(57) ABSTRACT

A method of producing a binding surface for a target molecule having a functional binding site, which method comprises: (i) identifying within the target molecule an anchor site which is remote from the functional binding site; (ii) generating a pharmacophore model for the anchor site; (iii) using the pharmacophore model to identify an anchor site binding ligand; and (iv) providing the anchor site binding ligand on a surface of a substrate such that the ability of the anchor site binding ligand to bind to the anchor site is preserved.

22 Claims, 3 Drawing Sheets

FOREIGN PATENT DOCUMENTS

| | | |
|---|---|---|
| CA | 2249955 | 4/2000 |
| EP | 0060138 | 3/1982 |
| EP | 0231918 | 2/1987 |
| EP | 0342068 | 4/1989 |
| EP | 0311989 | 1/1993 |
| EP | 0837080 | 4/1998 |
| EP | 0947544 | 10/1999 |
| EP | 0972566 | 1/2000 |
| EP | 1072635 | 7/2000 |
| GB | 0856329 | 12/1960 |
| GB | 0935013 | 8/1963 |
| GB | 1138287 | 12/1968 |
| GB | 02199786 | 7/1988 |
| JP | 1275639 | 11/1989 |
| JP | 3065341 | 3/1991 |
| JP | 8259716 | 8/1996 |
| JP | 2001-261758 | 9/2001 |
| WO | WO 90-02749 | 3/1990 |
| WO | WO 90-07575 | 7/1990 |
| WO | WO 91-07687 | 5/1991 |
| WO | WO 92-05696 | 4/1992 |
| WO | WO 95-09176 | 4/1995 |
| WO | WO 97-02310 | 1/1997 |
| WO | WO 97-47661 | 12/1997 |
| WO | WO 98-01480 | 1/1998 |
| WO | WO 98-31732 | 7/1998 |
| WO | WO 99-28352 | 6/1999 |
| WO | WO 00-12575 | 3/2000 |
| WO | WO 00-78740 | 12/2000 |
| WO | WO 01-62804 | 8/2001 |
| WO | WO 02-50171 | 6/2002 |
| WO | WO 03-000708 | 1/2003 |
| WO | WO 03-042249 | 5/2003 |
| WO | WO 2004-055518 | 7/2004 |

OTHER PUBLICATIONS

Turkova Oriented immobilization of biologically active proteins as a tool for revealing protein interactions and function Journal of Chromatography B vol. 722 pp. 11-37 (1999).*
Penzol et al. Use of Dextrans as Long and Hydrophilic Spacer Arms to Improve the Performance of Immobilized Proteins Acting on Macromolecules Biotechnology and Bioengineering vol. 60, pp. 518-523 (1998).*
International Search Report from priority patent application No. PCT/AU2004/001747, filed Dec. 10, 2004.
Daeyaert, F. et. al., "A Pharmacophore Docking Algorithm and its Application to the Cross Docking of 18 HIV-NNRTI's in their Binding Pockets", *PROTEINS: Structure, Function, and Bioinformatics*, vol. 54 (2004), pp. 526-533.
Zheng, Y. et. al., "Biosensor Immunosurface Engineering Inspired by B-cell Membrane-bound Antibodies: Modeling and Analysis of Multivalent Antigen Capture by Immobilized Antibodies", *IEEE Transactions on Nanobioscience*, vol. 2 (1) (2003), pp. 14-25.
Sackmann, E. et. al., "Supported Membranes on Soft Polymer Cushions: Fabrication, Characterization and Applications", *Tibtech February*, vol. 18 (2000), pp. 58-64.
Müller, K. et. al, "Model and Simulation of Multivalent Binding to Fixed Ligands", *Analytical Biochemistry*, vol. 261(1998), pp. 149-158.
U.S. Appl. No. 10/052,907 Non-final office action dated Jul. 27, 2005.
U.S. Appl. No. 10/451,720 Notice of Allowance dated Aug. 11, 2006.
U.S. Appl. No. 10/109,777 Non-final office action dated May 21, 2003.
U.S. Appl. No. 10/109,777 Notice of Allowance dated Dec. 5, 2003.
U.S. Appl. No. 10/514,070 Restriction Requirement dated Jun. 27, 2008.
U.S. Appl. No. 10/514,070 Restriction Requirement dated Dec. 12, 2008.
U.S. Appl. No. 10/451,807 Restriction Requirement dated Dec. 19, 2005.
Angot, S., et al., "Living Radical Polymerization Immobilized on Wang Resins: Synthesis and Harvest of Narrow Polydipersity Poly(methacrylate)s," Macromolecules, vol. 34, pp. 768-774 (2001).
Berg, R., et al., "Long-Chain Polystyrene-Grafted Polyethylene Film Matrix: ?A New support for Solid-Phase Peptide Synthesis," J. Am Chem. Soc., vol. 111, pp. 8024-8026 (1989).
Boer, B., et al., "Microporous Honeycomb-Structured Films of Semiconducting Block Copolymers and Their Use as Patterned Templates," Advanced Materials, vol. 12, No. 21, pp. 1581-1583 (2000).
Darling, T., et al., "Living Polymerization: Rationale for Uniform Terminology," J. Polym. Sci. Part A: Polym. Chem., vol. 38, pp. 1706-1708 (2000).
Derwent Abstract Accession No. 1991-127943 and JP-03-065341 (XP002394884).
Derwent Abstract Accession No. 2001-499482 and JP-2001-158847.
Derwent Abstract Accession No. 89-367670, Class A35, and JP 1-275639 A.
Derwent Abstract Accession No. 96-502794, Class A96, and JP 8-259716 A.
Ejaz, M., et al., "Controlled Grafting of a Wall-Defined Glyco-polymer on a Solid Surface by Surface-Initiated Atom Transfer Radical Polymerization," Macromolecules, vol. 33, pp. 2870-2874 (2000).
European Supplemental Partial Search Report of EP 01271412 dated May 13, 2004.
European Supplementary Search Report of EP 01271084 dated May 19, 2004.
European Supplementary Search Report of EP 02712637 dated Aug. 16, 2006.
European Supplementary Search Report of EP 03718551 dated Jul. 5, 2005.
European Supplementary Search Report of EP 05756657 dated Feb. 26, 2009.
Granel, C., et al., "Controlled Radical Polymerization of Methacrylic Monomers in the Presence of a Bis(ortho-chelated) Arylnickel(II) Complex and Different Activated Alkyl Halides," Macromolecules, vol. 29, pp. 8576-8582 (1996).
Hawker, C., et al., "Radical Crossover in Nitroxide Mediated 'Living' Free Radical Polymerizations," J. Am. Chem. Soc., vol. 118, pp. 11467-11471 (1996).
Hori, M., et al., "Investigating Highly Crosslinked Macroporous Resins for Solid-Phase Synthesis," Biorganic & Med. Chem. Letters, vol. 8, pp. 2363-2368 (1998).
International Preliminary Report on Patentability of PCT/AU2005/000966 dated Jan. 9, 2007.
International Search Report of PCT/AU01/01638 dated Jan. 22, 2002.
International Search Report of PCT/AU03/00566 dated Jul. 1, 2003.
International Search Report of PCT/AU2005/0009966 dated Aug. 3, 2005.
Jenekhe, S., et al., "Self-Assembly of Ordered Microporous Materials from Rod-Coil Block Copolymers," Science, pp. 372-375 (1999).
Karthaus, O., et al., "Water-Assisted Formation of Micrometer-Size Honeycomb Patterns of Polymers," Langmuir, vol. 16, No. 15, pp. 6071-6076 (2000).
Kato, M. et al., "Polymerization of Methyl Methacrylate with the Carbon Tetracloride/Dichlorotris-(triphenylphosphine)ruthenium(II)Methylaluminum Bis(2,6-di-tert-bu-tylphenoxide)Initiating System: Possibility of Living Radial Polymerization," Macromolecules, vol. 28, pp. 1721-1723 (1995).
Kunitake, T., "Self-Assembly of Polymers," Current Opinion in Colloid and Interface Sciences, vol. 6, pp. 1-2 (2001) Editorial Overview.
Machi, S., et al., "Effect of Swelling on Radiation-Induced Grafting of Styrene to Polyethylene," J. Polymer Science, vol. 8, pp. 3329, 3337 (1970).
Maeji, N. Joe, et al., "Grafted Supports Used with the Multipin Method of Peptide Synthesis," Reactive Polymers, vol. 22, pp. 203-212 (1994).
Mandal, T. et al., "Production of Hollow Polymeric Microspheres by Surface-Confined Living Radical Polymerization on Silica Templates," Chem. Mater., vol. 12, pp. 3481-3487 (200).

Maruyama, N., et al., "Mesoscopic Patterns of Molecular Aggregates on Solid Substrates," Thin Solid Films, 327329, pp. 854-856 (1998).

Muir, B.W., et al., "High-Throughput Optimization of Surfaces for Antibody Immobilization Using Metal Complexes," Analytical Biochemistry, vol. 363, No. 1, pp. 987-107 (2007) XP005910998.

Needels, M., et al., "Generation and Screening of an Oligonucleotide-Encoded Synthetic Peptide Library," Proc. Natl. Acad. Sci. USA, vol. 90, pp. 10700-10704 (1993).

Nishikawa, T., et al., "Honeycomb-Patterned Thin Films of Amphiphilic Polymers as Cell Culture Substrates," Materials Science and Engineering, C vol. 8-9, pp. 495-400 (1999).

Nishikawa, T., et al., "Mesoscopic Patterning of Cell Adhesive Substrates as Novel Biofunctional Interfaces," Materials Science and Engineering, C vol. 10, No. 1-2, pp. 141-146 (1999).

Ookura, R., et al., "Stabilization of Micropatterned Polymer Films as Artificial Extracellular Matrices for Tissue Engineering, Molecular Crystals and Liquid Crystals Science and Technology Section A-Molecular Crystals and Liquid Crystals," vol. 337, pp. 461-464 (1999).

Patel, D., et al., "Applications of Small-Molecule Combinatorial Chemistry to Drug Discovery," DDT, vol. 1, No. 4, pp. 134-144 (1996).

Patten, T. et al., "Polymers with Very Low Polydispersities from Atom Transfer Radical Polymerization," Science, vol. 272, pp. 866-868 (1996).

Percec V., et al., "Living Radical Polymerization of Styrene Initiated by Arenesulfonyl Chlorides and $Cu^1(bpy)_nCl$," Macromolecules, vol. 28, pp. 7970-7972 (1995).

Rich, R., et al., "Advances in Surface Plasmon Resonance Biosensor Analysis," Current Opinion in Biotechnology, vol. 11, pp. 54-61 (2000).

Rohr, J., "Combinatorial Biosynthesis—An Approach in the Near Future?" Agnew. Int. Ed. Engl., vol. 34, pp. 881-884 (1995).

Ruiz-Taylor, L., et al., "Monolayers of Derivaitzed Poly-L-lysine)-Grated Poly(ethylene Glycol) on Metal Oxides as a Class of Biomolecular Interfaces," PNAS, vol. 98, No. 3 pp. 852-857 (2001).

Schaaper, W., et al., "Synthesis of Large Numbers of Peptides for Rapid Screening of Bioactive Sequences," in J.A. Smith and J.E. River (Eds.), 12th American Peptide Symposium, Boston, MA, Jun. 16-21, 1991 Escom. Leiden, p. 651 (1992).

Shimomura, M., et al., "Bottom-up Strategy of Materials Fabrication: A New Trend in Nanotechnology of Soft Materials," Current Opinion in Colloid & Interface Sciences, (2001).

Stalmach, U., et al., Semiconducting Diblock Copolymers Synthesized by Means of Controlled Radical Polymerization Techniques, Journal of the American Chemical Society, vol. 122, pp. 5464-5472 (2000).

Stolowitz, M., et al.,"Phenylboronic Acid-Salicylhdroxamic Acid Bioconjugates, 1. A Novel Boronic Acid Complex for Protein Immobilization," Bioconjugate Chemistry, vol. 12, pp. 229-239 (2001).

Tregear, G., "Graft Copolymers as Insoluble Supports in Peptide Synthesis," Chemistry and Biology of Peptides: Meienhofer, J., Ed., Ann Arbor Sci. Publ: Ann Arbor, MI, p. 175-178 (1972).

Wang, J., et al., "Controlled/'Living' Radical Polymerization. Atom Transfer Radical Polymerization in the Presence of Transition-Metal Complexes," J. Am. Chem. Soc., vol. 117, pp. 5614-5615 (1995).

Widawski, G., et al., Self-organized honeycomb morphology of starpolymer polystrene films, Nature, vol. 369, pp. 387-389 (1994).

Written Opinion of PCT/AU2005/000966 dated Aug. 18, 2005.

Zhao, C., et al., "Polystyrene Grafted Fluoropolymer Micro Tubes: New Supports for Solid-Phase Organic Synthesis with Useful Performance at High Temperature," J. Combinatorial Chemistry, vol. 1, pp. 91-95 (1999).

U.S. Appl. No. 10/514,070 Final office action dated Jun. 22, 2010.

U.S. Appl. No. 10/514,070 Advisory Action dated Aug. 25, 2010.

U.S. Appl. No. 11/571,422 Restriction Requirement dated Feb. 3, 2010.

U.S. Appl. No. 11/571,422 Restriction Requirement dated May 19, 2010.

U.S. Appl. No. 11/571,422 Non-final office action dated Sep. 1, 2010.

Gold, E.R., et al., "Chromic Chloride: A Coupling Reagent for Passive Hemagglutination Reactions," The Journal of Immunology, vol. 99, No. 5, pp. 859-866 (1967).

Penzol, et al., Use of Dextrans as Long and Hydrophilic Spacer Arms to Improve the Performance of Immobilized Proteins Acting on Macromolecules Biotechnology and Bioengineering, vol. 60, pp. 518-523 (1998).

* cited by examiner

FIGURE 3
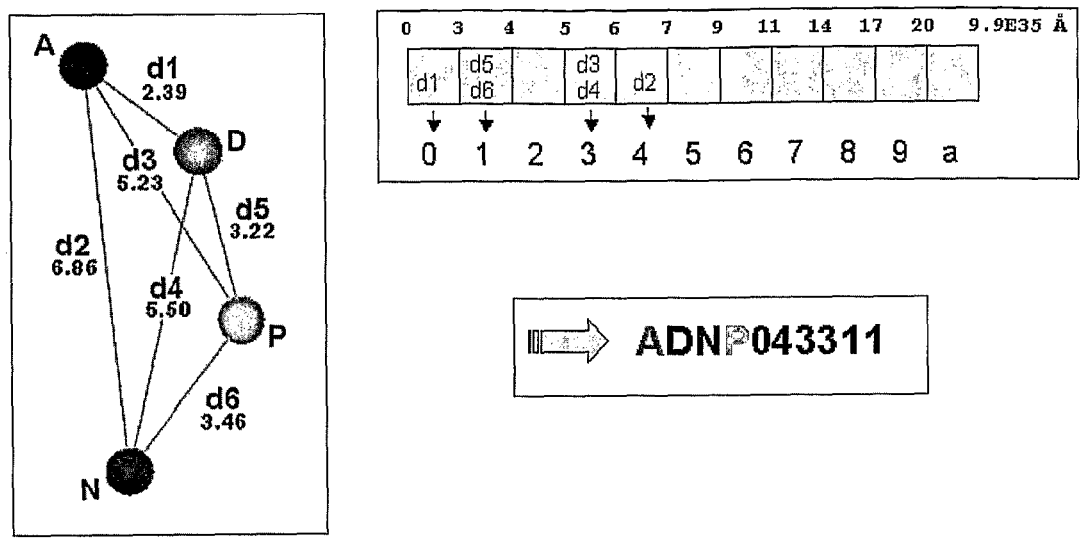
FIGURE 4A
FIGURE 4B
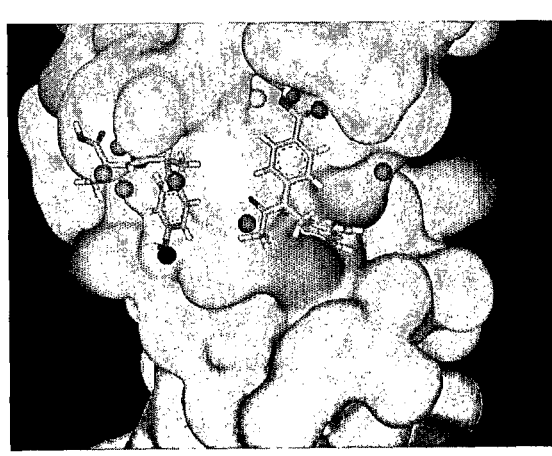
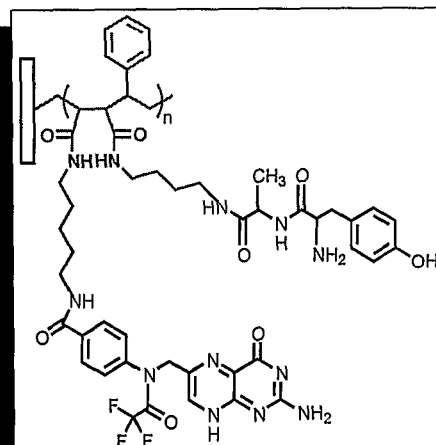

METHOD FOR DESIGNING SURFACES

This application is a National Stage of International Application PCT/AU04/001747, filed Dec. 10, 2004, which published as WO 05/057462 A1 on Jun. 23, 2005 under PCT Article 21(2) in English, and which claims the priority of U.S. Provisional Patent Application No. 60/529,605, filed Dec. 12, 2003, each of which is hereby incorporated by reference herein.

The present invention relates to a method of designing a substrate surface which has desirable properties in terms of its ability to bind or capture target molecules of interest. More specifically, the present invention relates to a computer implemented method for molecular modelling of surface coatings, the characteristics of which are designed to bind molecules in some preferred orientation. The invention also relates to a method of producing such surfaces involving the method of design, and to surfaces when so-produced.

BACKGROUND

In the life sciences, isolation of specific biomolecules of interest from complex mixtures and assays to identify those molecules and their interacting partners are commonplace. Such methods tend to be performed on solid phase substrates, normally made of glass, silica, or plastics, such as polypropylene and polystyrene, and to increase throughput and improve efficiency, these substrates are typically used in the form of small beads, columns, microscope slides, multi-well plates or membranes. The basic assumption has always been that the surface characteristics of the substrate does not seriously affect the various interactions that are required to take place during the screening or separation process. However, this is not necessarily the case and the lack of suitable solid phase substrates has lead to non-optimal processes and, in some cases, failure of the processes to work at all. For example, in immunoassays, it is well known that immobilization or coupling of peptide or protein antigens on plastic substrates such as latex beads and polystyrene multi-well plates can lead to conformational changes in the antigen resulting in poorer than expected binding with the antibody and sometimes complete failure in the assay (Kabat, E. A., Basic principles of antigen-antibody reactions, in Methods of Enzymology, Vol. 70, Colowick, S. P., and Kaplan, N. O., Eds., Academic Press., New York, 1980, P3; Dierks, S. E., Butler, J. E., and Richerson, H. B., Altered recognition of surface adsorbed compared to antigen bound antibodies in the ELISA, Mol. Immunol., 23, 404, 1986) The opposite situation also exists in that a weak intrinsic interaction between an immobilised antigen and antibody may be converted into a strong interaction in a ternary complex of antigen, antibody and solid phase matrix (Stevens, F. J., "Considerations of the interpretation of the specificity of monoclonal antibodies determined in solid phase immunoassays (Chapter 13, P239, last paragraph in CRC Immunochemistry of Solid Phase Immunoassays, 1991). Between the two extremes of no/poor binding when there is supposed to be high binding affinity and high affinity binding when the reality is low binding affinity (false positives in solid phase screening methods) there is an enormous variation of outcomes that are dependent on the biomolecule being immobilised and the solid phase material. The kinetics of solid phase interactions differ significantly from classical liquid phase interactions and there is no rational process to relate the two interactions when the influence of the solid support becomes significant (see for example Kabat, E. A., Basic principles of antigen-antibody reactions, in Methods of Enzymology, Vol. 70, Colowick, S. P., and Kaplan, N. O., Eds., Academic Press., New York, 1980, P3; Karush, F., The affinity of antibody: range, variability and the role of multivalence, in Comprehensive Immunology, Vol 5, Litman, G. W. and Good R. A., Eds., Plenum Press, New York, 1978, P85; Franz B. and Stegemann, M., The kinetics of solid phase microtiter immunoassays, CRC, 1991, Ch. 18, P277)

Rather than solve this challenging problem of solid phase effects, current strategies normally try to avoid the issue altogether. A common strategy has been to identify surface coatings with minimal "non-specific" binding but with the potential to covalently bind capture agents that are subsequently used to capture their complementary binding molecules.

For example, an important category of capture agents for separations and assays are antibodies and there are a number of methods to immobilize antibodies onto a substrate (see Ed Harlow and David Lane; Antibodies: A laboratory manual by Cold Spring Laboratory, (1988)). Covalent attachment of antibodies to a solid substrate surface can be categorized into three broad classes, as follows.

In the first class, protein A or protein G is first covalently attached to a substrate to act as a capture molecule for the antibody. The antibody requires this capture molecule to bind it to the substrate surface and this interaction is stabilized by cross-linking with a bifunctional coupling reagent such as dimethylpimelimidate (DMP). As both protein A and protein G bind to the Fc region of the antibody, the antigen binding site of the bound antibody will be oriented correctly for optimal subsequent interaction with antigens. This technique tends to be expensive and initial coupling of protein A or protein G onto the solid support is random, leading to uncontrolled orientation and non-optimal antibody loading due to a limited number of protein A or G molecules being bound to the substrate in an orientation which is suitable for antibody binding.

A second type of coupling method uses substrate surface coatings having reactive groups that directly couple certain amino acid side chains in the antibody such as lysine. The main disadvantage of this approach is the lack of control on which lysine(s) in the antibody is/are coupled to the substrate surface. Poor orientation and damage to the antibody are likely outcomes.

A third technique involves activating the antibody first and then coupling the antibody onto a substrate having some reactive groups on its surface. This technique has the same disadvantages as the previous method except when periodate is used to activate the antibody. The periodate breaks the sugar rings in the Fc region and allows the antibodies to be coupled to the substrate bound reactive groups such as amines. In this case, orientation of the antibody can be controlled.

In the prior art, there are many examples on the use of small molecule ligands to bind or capture proteins. For example, the strong binding affinity of biotin to streptavidin can be used. However, if biotin is coupled onto the substrate surface then the antibody needs to be fused or coupled to the streptavidin sequence which greatly complicates the process.

As another example, glycogen synthase kinase-3 (GSK-3) inhibitors have been coupled onto substrate surfaces to identify their actual intracellular targets (Knockaert et al., Identification following affinity purification on immobilised inhibitor, J. Biol. Chem. 2002 277:25493-25501). As another example, Schreiber et al. have synthesized a library of over 2 million unique chemical compounds on small latex beads to screen against cells and multiple proteins. The researchers also claimed printing such compounds on to glass slides, creating small molecule microarrays to probe potential protein targets (Target-oriented and diversity-oriented organic synthesis in drug discover; Science 2000, 1964-1969). However, the experience of most laboratories is that the ligands identified from screening some kind of library invariably binds to native interaction regions of the target protein. If the objective is to orient such interaction regions of the target protein, then existing approaches are very limiting.

As well, just because a protein is bound to the substrate surface through some small molecule ligand does not necessarily mean that the protein will remain in its preferred orientation and conformation. As mentioned before, non-optimal surfaces can lead to conformational changes in the protein resulting in poorer than expected signal to noise ratio and sometimes complete failure in the assays.

Whether by covalent coupling or non-covalent immobilization, there is a need to develop synthetic surface coatings that stabilize and maintain a biological molecules such as antibodies in some preferred orientation. The use of another biological molecule (e.g. protein A) to orient the target molecule (e.g. antibody) only shifts the problem.

There are now a number of highly parallel or combinatorial processes that can potentially generate millions of ligands and identify potentially useful leads. The earliest version of such concepts is that of Mario Geysen who describes methodologies to identify peptide ligands using antibodies to "select" from a large number of peptides, those peptides which bound the antibody. One version was an incremental strategy where a set of 400 dipeptides were immobilised on individual solid supports and tested for their binding affinity. The leads were progressively "built up" to identify higher binding ligands of tri-, tetra- and longer peptides until the appropriate degree of complementarity as judged from the binding characteristics was achieved (see Geysen, H. M., Rodda, S. J. and Mason, T. J., A priori delineation of a peptide which mimics a discontinuous antigenic determinant, Mol. Immunology, 23, 709-715, 1986; Geysen, H. M., Antigen-antibody interactions at the molecular level: adventures in peptide synthesis, Immunology Today, 6 1985, 364-9). In this case, good binding characteristics on the solid phase did not necessarily mean that there was good binding of the peptide ligand in solution or good binding when the ligand was transferred to another solid phase. The surface factors were not part of the discovery process.

More recently, published International patent application WO 03/095494 describes a way of assembling a large library of molecular coatings. In brief, this application describes polymeric surface coatings of the formula B-S-F, where B is a copolymer of at least one passive constituent P and at least one active constituent A, S is a spacer unit and F is a chemical or biological functional group, wherein S is attached to the active constituent A of copolymer B, and wherein the coating has at least one point of diversity selected from P, A, S and F. The functional group F can be a site for further diversity or a group capable of binding or chemically reacting with some biological molecule.

The ability to generate a vast number of different surface coatings of peptide, small molecule or other ligands does not in itself increase the success rate of identifying useful surfaces. Key solid phase applications not only require surfaces with high and low non-specific binding capabilities but also specific binding characteristics that may preferentially orient a target molecule such that some other part of the molecule is freely accessible for subsequent interaction with its complementary binding molecule. Another example in bio-separations is specific high binding capacity but efficient release under some slightly different conditions, e.g., pH or salt change. To efficiently identify such surface coatings, there must be some design elements to complement the capability to assemble and screen millions of surfaces.

Computational chemistry, which incorporates a variety of different methods developed and applied since the early 1980s, is now a well-established approach to identifying new drug leads in the pharmaceutical industry. The main focus has been on generating methodologies and computer programs to design potential small molecule compounds that would bind into a protein binding site or prevent a protein-protein interaction. Biological and chemical databases, virtual screening, pharmacophore modelling, 3-D molecular modelling, QSAR, structural prediction of homologous proteins, to cite a few, are routinely used techniques and have successfully led to the design of new drugs such as HIV protease inhibitors for treating AIDS (Leon et al.; Approaches to the design of effective HIV-1 protease inhibitors, Curr. Med. Chem., 2000, 7, 455).

At the early stage of drug design, computational chemists improve decision-making and help to accelerate the discovery process by increasing the speed and decreasing the cost of identifying lead compounds. This can be achieved by eliminating unpromising compounds and/or by identifying ones which fulfill some criteria that have been identified as important for biological activity. This virtual screening can be performed mainly by using QSAR type models, pharmacophore models, and/or docking techniques. There are many variations on the theme and the choice of the techniques and all their combinations will mainly depend on the number of candidate molecules to be virtually screened and on the knowledge of the target. In brief, the approach involves selecting compounds that fit a feature, a ligand or a receptor.

Assembling and identifying surfaces with the correct set of functionalities in their correct spatial distribution for any particular target protein is a time consuming process. While computational methods are well established in drug discovery, design of ligands for surface discovery has unique requirements that make the end goals very different. In drug discovery, the focus is on identification of high affinity ligands with "drug-like" characteristics in terms of their oral availability, toxicity, etc. As discussed, the solid phase is effectively a tertiary component of the solid phase assay. Even if the strategy is covalent coupling to immobilise some biomolecule to some surface, the effective binding energies after incubation for 16 hrs can be >80% due to non-covalent surface interactions (see CRC Immunochemistry of Solid Phase Immunoassays, J. E. Butler Ed. Chapter 1, p 11).

Some of the differences between designing surfaces for discovery purposes and computational methods in drug discovery are as follows;

a. The ligands responsible for binding a molecule of interest to a surface are actually part of the surface itself and since they are binding macromolecules that are far larger, the binding contributions of the remaining components of the surface must also be considered in the design process.

b. Unless the biomolecule being immobilised on a surface is a spheroid having uniform surface characteristics, it is unlikely that there is random orientation in respect to a specific solid phase. The opportunity to design ligands that preferentially target certain regions of the target biomolecule also means that the design process can incorporate features that preferentially do not target other regions.

c. It is certain that multiple modes of association exist between the incoming biomolecule, small molecule binding ligands and other surface components. As the ligands are part of a contiguous surface, different pharmacophore ligands targeting different sections of an overall binding site on a biomolecule can be incorporated into the surface without the need to achieve some arbitrarily chosen affinity goal.

There is an opportunity to design small molecule binding ligands as an integral part of the surface component and additionally tune surface characteristics to an intended application.

To address these challenges, the present invention seeks to provide computer-based methods for designing structural features on an artificial surface to capture and manipulate the orientation of different molecules, such as protein classes, and where the surface coating can preferentially enhance specific orientation of those molecules. With respect to the life sciences, these methods are intended to enable identification of optimised surfaces for new bioassays as well as greatly improve the performance in existing bioassays.

SUMMARY OF PRESENT INVENTION

In one embodiment, the present invention provides a method of designing a binding surface for a target molecule having a functional binding site, which method comprises:
(i) identifying within the target molecule an anchor site which is remote from the functional binding site;
(ii) generating a pharmacophore model for the anchor site;
(iii) using the pharmacophore model to identify an anchor site binding ligand; and
(iv) providing the anchor site binding ligand on a surface of a substrate such that the ability of the anchor site binding ligand to bind to the anchor site is preserved.

In the context of the present invention the term "target molecule", and variations thereof such as "target protein", refers to a molecule which is bound to a substrate surface in some preferred orientation so that the molecule has the ability to undergo a subsequent binding interaction with another molecule of interest. In the present specification the molecule of interest is termed a "complementary binding molecule". By way of illustration, in a biological assay, the target molecule may be an antibody and the complementary binding molecule an antigen.

As will be explained, the present invention uses molecular modelling techniques in order to design a substrate surface which has the potential to bind target molecules to maximise a predetermined orientation of those molecules. The ability to control the orientation of such molecules provides advantages in terms of sensitivity and resolving power when the surface is used subsequently in order to utilise subsequent binding interactions of that molecule which are orientation dependent, such as to bind a complementary binding molecule of interest. As explained, conventional techniques for providing target molecules on a substrate are somewhat hit and miss in this regard. When compared to such techniques the surfaces designed in accordance with the present invention may have the ability to bind a higher proportion of target molecules that more effectively bind to complementary binding molecules. This comes down to the ability to control the orientation of a target molecule on a substrate surface through surface design so that the target molecule is suitably orientated for subsequent binding interaction with its complementary binding molecule. The present invention may enable a binding surface to be designed that has the ability to selectively capture (and thus remove) biological molecules, such as proteins, from a mixture containing the biological molecules and other species. This capture occurs as a result of preferential binding interaction between the binding surface and a selected region of the target molecule (or molecules) of interest. The selectivity of this binding interaction (as opposed to binding with other regions of the target molecule) also implies that the binding surface will not interact with other biomolecules within the mixture. In summary, such design capabilities increase the likelihood of identifying surfaces that have selectivity to a target molecule as opposed to other molecules. Additionally or alternatively, the present invention may be applied to provide suitable binding to a target molecule under certain environmental conditions, but not under other conditions such as changes in pH and ionic strength.

The invention also provides a method of producing a substrate including a target molecule bound to its surface in a predetermined orientation, the substrate having been designed in accordance with design method of the invention as described herein. The invention further provides substrates which have been designed in accordance with this method of design, and their practical application. This provides the opportunity to control binding events by manipulation of environmental conditions.

DETAILED DISCUSSION OF THE PRESENT INVENTION

The present invention will be described with particular reference to designing polymeric surfaces that preferentially bind biological target molecules such as proteins. More specifically, the surface design techniques of the present invention are targeted at antibodies as the target molecule with the intention of achieving antibody binding in a predetermined orientation. In turn, this increase sensitivity in immunoassays. However, it will be appreciated that the underlying concepts of the present invention may be applied to the design and manufacture of different types of surface which are required to immobilise other types of target molecule in some preferred orientation. This said, it is envisaged that the present invention will have primary applicability to the design of synthetic biomimetic surface coatings.

For the purposes of the invention, the target molecule which it is intended to be immobilized to a substrate surface has two distinct types of binding site which are referred to herein as an anchor site and a functional binding site. The function and relative position of these sites is fundamentally important in the present invention. The anchor site facilitates attachment of the target molecule to the binding substrate/ substrate surface thereby enabling the target molecule to be immobilised for some specific assay. The functional binding site is responsible for the target molecule having some desired functionality by enabling the target molecule to undergo a binding interaction with its complementary binding molecule while immobilised on the substrate. Alternatively, the functional binding site can be a binding site used to indicate that the target molecule has been bound to the substrate. For the purpose of the invention, there can be two or more different or similar functional binding sites and it is also possible that an anchor site in one context may be a functional binding site in another context.

The interaction between the target molecule and its complementary binding molecule is specific to the functional binding site and this means that when the target molecule is bound to at least part of the substrate, the functional binding site must be orientated in such a way as to be available for subsequent interaction with its complementary binding molecule. This has implications with respect to the relative position of the anchor site and functional binding site on the target molecule, and herein the term "remote" is intended to mean that the spatial positioning of these sites within the target molecule is such that the ability of the functional binding site to interact as desired is preserved when the target molecule is immobilised on a substrate via the anchor site. The term "remote" is not intended to mean that the anchor site and functional binding site are positioned on "opposing sides" of the target molecule, although this is obviously a possibility. The anchor site and functional binding site may occupy any position relative to each other provided the desired binding potential of the functional binding site remains intact. In the context of an antibody as a target molecule, the Fab fragment corresponds to the functional binding site. The anchor site may be located on the Fc fragment of the antibody.

The first step of the method of the invention involves identifying within the target molecule an anchor site in order to enable the target molecule to be attached to the surface of a substrate. The extent to which the target molecule is bound to the substrate surface must be sufficient such that the target molecule is not accidentally displaced during practical application of the surfaces designed and produced in accordance with the present invention. In principle, it is possible that the required degree of binding may be achieved through one anchor site binding ligand in combination with non-specific binding of other surface components. Generally, however, the interactions which facilitate binding of the target molecule to the substrate through its various surface components are relatively weak and this means that binding may require interaction between a number of anchor site binding ligands with complementary anchor sites of a single target molecule to achieve suitable immobilisation of the target molecule. Typically, each anchor site binding ligand will have specificity for a single anchor site so that the anchor site binding ligands are different from each other. Thus, subject of course to context and other non-specific binding components that may be present on the surface, references herein to a single ligand or a single anchor site should be read as also meaning at least two such ligands or sites.

The location of suitable anchor sites is predicated by the location within the target molecule of the functional binding site, and this in itself will be known for the target molecule of interest. Indeed, the target molecule will be selected based on the nature of this site and, more specifically, on the complementary binding molecule to which the functional binding site has binding specificity. It is possible based on the location of the functional binding site to determine possible anchor sites which will provide the functional binding site in a suitable orientation when the target molecule is immobilised on a substrate surface. In practice, potential anchor sites may be identified based on an understanding of the molecular architecture of the target molecule and on the binding characteristics of the functional binding site, both of which may be well documented for a given target molecule.

The experimental 3-D structure of the target molecule obtained by x-ray diffraction or NMR spectroscopy techniques is possibly the best source of information for this step of the modelling. Both published and proprietary databases may be used in this regard. For instance, the Protein Data Bank (PDB) is the largest worldwide repository for the processing and distribution of 3-D structure data of large molecules such as proteins. In the absence of such experimental structure, homology modelling may generate a software-based 3-D model of the target molecule. For example, for a target protein this may be done using its amino acid sequence and relating that to the structures of known proteins.

It may also be appropriate to undertake a bioinformatic search of relevant databases to search for the presence of potential anchoring sites. For example, public or proprietary databases of protein motifs or domain such as NCBI Dart, Smart, Pfam, Prosite, Interpro or Blocks may provide data and tools to identify which domains are present within the target molecule (Marchler-Bauer et al., CDD: a database of conserved domain alignments with links to domain three-dimensional structure. Nucleic Acids research 30 281-283 (2002)). Analysis of protein-protein interaction screening data experimentally generated, for example, using yeast two-hybrid screens, may also provide information on which anchoring sites are present within the target molecule.

Possible anchor sites may also be identified by computer modelling of the 3-D structure of a given target molecule. One skilled in the art would be familiar with sources of such information and with the kind of computer hardware/software that may be employed. However, while ligand active sites can be identified, for example, by use of the Grid, MCSS, superstar, Q-fit programs or the Sphgen module from the Dock computer programs suite, identifying binding sites on a protein surface is recognized as being a difficult task. Indeed, it has been shown that a binding site present at the surface of a protein may be practically indistinguishable from other patches on the protein surface. Palma et al., (BiGGER: a new (soft) docking algorithm for predicting protein interactions; Proteins, 2000 Jun. 1; 39(4):372-84) describe the use of BiG-GER, a soft docking algorithm for predicting protein interactions based on the three-dimensional structures of unbound molecules. Recently, Ma et al., (Protein-protein interactions: Structurally conserved residues distinguish between binding sites and exposed protein surfaces, PNAS 2003 100: 5772-5777) have demonstrated that the use of polar residue hot spots can be used to determine potential binding regions.

Not all possible anchor sites identified in this step may ultimately be useful for binding the target molecule to the substrate surface and it is therefore usually necessary to identify a number of different anchor sites at various locations on the target molecule. This also affords design flexibility. Thus, any anchor site binding ligands that are identified as candidate ligands for binding of the anchor site of the target molecule but that would also result in binding at the functional binding site of the target molecule may be dismissed from further consideration.

Subsequent to identifying a suitably positioned anchor site on the target molecule, the method of the invention involves generating a pharmacophore model for that anchor site. In the context of the present invention the pharmacophore model is a set of spatially distributed properties or feature types that are likely to be responsible for the ability of a binding site (in this case the anchor site) to undergo some form of binding interaction. The pharmacophore model involves molecular features that relate to any form of interaction through which a binding site has binding potential, for example, hydrophobic, electrostatic and hydrogen-bonding interactions. The pharmacophore model characterises a particular binding site by reference to such molecular features.

The pharmacophore model is a 3-D representation of molecular features and, as such, must be defined by reference to at least four centres (spatially distributed properties). It may aid flexibility of design to use pharmacophore models that are characterised by more than four centres as this brings with it a greater number of candidate anchor site binding ligands which may interact with the anchor site as required.

The pharmacophore model can be generated by reference to the molecular features of the binding site itself and/or by reference to the molecular features of a set of one or more ligands already known to bind to the anchor site of interest. One skilled in the art would be aware of sources of information concerning complementary ligands for a given anchor site of a target molecule. For example, a number of online resources are available for protein-protein interactions. The Biomolecular Interaction Network Database (BIND) stores descriptions of interactions and molecular complexes such as between proteins, nucleic acids and small molecules. The Dictionary of Interfaces in Proteins (DIP) is another resource on interacting protein surfaces.

Numerous techniques for generating a pharmacophore model are known in the art and the invention does not reside in the selection of any particular technique. By way of example mention may be made of the following methodology and/or software systems: Catalyst; Ludi, DISCO; HipHop; GASP, Chem-X, Think and HypoGen. One skilled in the art would have no difficulty in using any of the known techniques in the context of the present invention.

Once a pharmacophore model has been generated for an anchor site the method of the invention involves using the pharmacophore model to identify an anchor site binding ligand. The intention here is to identify a ligand which maps or fits the pharmacophore model to some extent and which therefore has potential to bind to the anchor site. Previously cited programs and others available in the art can be used to perform the virtual screening. An important aspect of the present invention is that the ligand does not have to match precisely the full pharmacophore model to be considered as a "hit" if the model is defined by reference to a large number of centres. At the very least the ligand must match the pharmacophore model with respect to at least four centres thereof in order to have potential to bind to an anchor site characterised by the model. Thus, if the pharmacophore model has been defined by reference to a large number of centres, it will be appreciated that the number of potentially useful ligands that may be identified against the model will be increased. It will also be appreciated that if the pharmacophore model is defined by reference to a large number of centres, it may be possible to rank the likelihood of ligands exhibiting the necessary binding interaction based on the number of centres which the ligand matches. A ligand which matches a pharmacophore model with respect to a large number of centres is likely to be more suitable than a ligand which matches the model in a more limited way.

With respect to this step of the method of the present invention it may be useful to resort to compound databases which generally correspond to a corporate collection of physically available compounds or compounds available externally from chemical compound suppliers. In this latter case, two types of libraries can be used. The first type originates from molecules that can be bought on a one-at-the-time basis. Individual supplier catalogue of compounds can be used or compilations such as the MDL's ACD (Available Chemicals Directory) or CambridgeSoft's ChemACX might be a more comprehensive source. For example, the ACD is a structure-searchable database of commercially available chemical compounds, with pricing and supplier information for over a quarter of a million research-grade and bulk chemicals from over 600 suppliers worldwide. The second type of library is a screening library from screening compound collection suppliers where the full library or part of it can be acquired. Compilations of screening libraries are also available like the MDL Screening Compounds Directory or CambridgeSoft's ChemACX-SC. Another source of information might be a virtual library corresponding to compounds generated by computer software (CombiLibMaker, Legion) from a list of reagent and a given chemistry.

Molecular modelling software and techniques known in the art may also be used to translate a particular pharmacophore model into suitable ligand structures. Ludi is an example of a program that offers a de novo technique that has been recently extended to work with larger databases of flexible molecules. Techniques known in the art for performing this particular step are well suited to designing relatively small ligands (molecules) and they cannot readily be extended to the design of surface biomimetics. The main reason for this is the nature of the binding interactions involved in the binding event for a given binding site. For proteins, at least, the average contact area is 800 $Å^2$ and molecules that could complement such a large surface area are generally rare. For example, the average contact surface area offer to a protein surface by a set of 7,595 commercial mono-carboxylic acids is about 130 $Å^2$ with a standard deviation of 55 $Å^2$. Furthermore, molecules in the high range of surface area generally have a large number (in excess of 15) rotatable bonds (excluding terminal groups) and it is either not possible or not practical to use current pharmacophore methodologies for processing the vast array of possible configurations that this brings with it. Thus, the anchor site binding ligands generated in this step are relatively small and simple molecules. In practice it is expected that other surface components will contribute to the total binding energy that results in immobilisation of a target molecule as required.

In reality it is not guaranteed that an anchor site binding ligand identified in accordance with the present invention will bind as desired to an anchor site. For instance, part of the ligand may collide with residues of the anchor site or one or more structural features in the candidate ligand may be incompatible with one or more functional groups of the anchor site. The technique which is adopted generates candidate ligands and the method of the invention preferably also includes a docking step to ensure binding efficacy of an anchor site/ligand pair. This also allows ligands to be ranked according to binding affinity for an anchor site.

Docking may be performed by various techniques known in the art such as Dock, FlexX, Slide, Fred, Gold, Glide, AutoDock, LigandFit, ICM, QXP. In the present invention, the at least four centres of the pharmacophore model are used to position the candidate ligand onto the anchor site. Then an extensive conformational search may be used to generate all potential configurations that are acceptable in terms of steric constraints. Scoring of the resulting generated complexes can be performed using either physical-based, empirical or knowledge-based scoring functions. Physical-based scoring functions are based on atomic force fields such as Amber or CHARMM. Empirical scoring functions such as Score or Chemscore are based on physico-chemical properties such as hydrogen-bond counts and use several energy terms that approximate for example hydrogen bonding, hydrophobic interactions and entropic changes to estimate the binding free energy. The coefficient used in each term are derived from fitting to known experimental binding energies for a variety of different protein-ligand complexes. Knowledge-based scoring functions, such as PMF or Drugscore are based on a statistical analysis of protein-ligand complexes. An individual free energy term associated with an interatomic contact may be determined from its frequencies in the database. The total binding free energy is calculated by the sum of individual free energies of interatomic contacts. The various types of scoring function can be used to perform an energy minimisation of the complex structure. The minimiser will adjust the position, orientation and exact conformation of the ligand within the anchor site. The flexibility of the target molecule or its anchor site may also be taken into account. With the first type of scoring function, molecular dynamic simulations with explicit solvent can be carried out and free energy perturbation (FEP) or thermodynamic integration (TI) methods generally give a good estimation of the binding free energies. It is to be noted that the optimised complex may no longer fit the pharmacophore centres that were initially used to position the ligand. The result is an anchor site binding ligand which is predicted to bind to the anchor site.

The interaction between the anchor site and the complementary anchor site binding ligand is relatively weak and this means that alone, it is likely to be insufficient to immobilise the target molecule on the surface of a substrate. Thus, in practice, it may be necessary to identify a number of anchor sites and complementary anchor site binding ligands for a single target molecule. The number of anchor site/ligand binding pairs that will be required will depend on the precise nature of the relevant interaction for a given pair and the sum of such interactions for all binding pairs involved. In practice whether one has identified an appropriate number and type of anchor site/ligand binding pairs for a given target molecule may be determined by assessing whether the capture molecule is suitably immobilised on a chosen substrate.

The next step of the method of the present invention involves providing the anchor site binding ligand on the surface of a substrate. The ligand must be immobilised on the surface so that the target molecule may itself be immobilised. When multiple ligands are involved, the ligands may be provided on the substrate surface with a suitable spatial distribution such that the ligands are suitably positioned to facilitate binding to the respective anchor sites of the target molecule. Thus, the spatial distribution of the individual anchor sites on the target molecule may also be an important consideration as this will dictate the relative position of the respective anchor site binding ligands required on the substrate surface. One way of doing this is by including the anchor site binding ligands as suitably positioned pendant groups on a backbone molecule which is bound to the substrate surface. Here the backbone molecule serves to (indirectly) attach the anchor site binding ligands to the substrate in an orientation which will enable subsequent binding of each ligand to its complementary anchor site. Molecular modelling techniques may be used to design suitable backbone molecules. It will then be necessary to consider which designed structures may be constructed in practice by techniques known in the art. Of course, when provided on the backbone the pendant anchor site binding ligands must retain the ability to bind to the anchor site(s) of interest. This can be verified by screening using techniques mentioned herein. Another way of ensuring that the anchor site binding ligands are suitably positioned is to provide the ligands at a high density on or at the surface of the substrate.

The fact that the anchor site binding ligands are small molecule compounds greatly increases the likelihood of being able to provide them with the correct spatial distribution on the substrate surface. In the prior art, low affinity ligands identified through experimental means have been tethered together through flexible linkers to form higher affinity ligands (D. J. Maly, et al. Combinatorial target guided ligand assembly: Identification of potent subtype-selective c-Src inhibitors., Proc. Natl. Acad. Sci., 97, 2000, 2419-2424; S. B. Shuker, et al., Discovering high-affinity ligands for proteins: SAR by NMR, Science, 274, 1996, 1531-1534.) However, the focus of such work was to develop small molecule drug candidates and not polymeric coatings. Also, Lacroix et al (Lacroix, M., Dionne, G., Zrein, M., Dwyer, R. J. and Chalifour, R. J. "The use of synthetic peptides as solid phase antigens" Chapter 16 in CRC Immunochemistry of Solid Phase Immunoassays, J. E. Butler, Ed., 1991), describe that the use of synthetic peptide antigens that ideally represent only the minimal size necessary to mimic a given antigenic determinant resulted in an increase in the density of epitope which could be coated on a solid phase. One advantage of this high epitope density was that it lead to bivalent attachment of antibodies—a condition that could result in a 1000-fold increase in functional affinity (avidity) relative to monovalent antibody attachment.

The substrate may be formed of any material conventionally used in the intended field of application. For example, the substrate may be glass, silica or plastic. Suitable plastics materials include: nitrocellulose; polyolefins such as polyethylene, polypropylene and polymethylpentene; polystyrene or substituted polystyrenes; fluorinated polymers such as poly (tetrafluoroethylene) and polyvinylidene difluoride; polysulfones such as polysulfone and polyethersulfone; polyesters such as polyethylene terephthalate and polybutylene terephthalate; polyacrylates and polycarbonates; and vinyl polymers such as polyvinylchloride and polyacrylonitriles.

The substrate may take any form. In biological applications the substrate will usually be in the form of beads, membranes, multi-well plates, slides, capillary columns or any other format that is used for biological assays, affinity separations, diagnostics or other applications where biological molecules are immobilised on some insoluble material (solid support).

Depending upon the chemical functionality available to attach the anchor site binding ligand(s) to the substrate, it may be appropriate to functionalise the substrate to facilitate suitable coupling of the anchor site binding ligand. Obviously, the latter must be attached to the substrate in such a way that its ability to undergo a suitable binding interaction with an anchor site of a target molecule is preserved. By way of example, if the anchor site binding ligand includes a carboxylic acid functionality available for coupling the ligand to the substrate, it may be appropriate to derivatise or modify the surface of the substrate in some way to enable coupling of the ligand through this carboxylic acid functionality. This may be achieved by coating of the substrate with a material that is reactive towards the carboxylic acid functionality of the anchor site binding ligand. It is of course necessary to assess the effect of such coating on the intended binding interaction between the anchor site binding ligand and an anchor site of a target molecule, and this may be done experimentally, as described herein. By way of illustration, when the anchor site binding ligand includes a carboxylic acid functionality available for coupling of the ligand to the substrate, the substrate may be coated with polyethyleneimine the amino groups of which are able to react with the carboxylic acid functionality of the anchor site binding ligand.

In an embodiment of the present invention the anchor binding site ligands may be designed to be incorporated within the repeat units of a polymer that forms, or is provided on, the substrate surface. The polymer may form the substrate itself or the polymer may be provided on at least a part of the surface of the a substrate formed from a different material. In its simplest form, the polymer is a homopolymer. Assuming multiple anchor site binding ligands are involved, the polymeric repeat unit will have at least two points of diversity based on the nature of the anchor site binding ligands which are included. The characteristics of the repeat unit may be derived from the monomers from which the polymer is formed, although the polymer may be formed and then modified to include pendant anchor site binding ligands which impart desirable non-covalent binding properties. In the latter case the polymer must of course include reactive functionalities to enable subsequent reaction to introduce the anchor site binding ligands.

The anchor site binding ligands that bind to the target molecule may be components of different repeat units in the polymeric chain but it is also possible that the ligands are within one repeat unit of the polymeric chain.

In one preferred embodiment, the polymer may be a copolymer of first and second monomers as described in published International patent application WO 03/095494. Here, examples of the first monomer include styrene (optionally substituted), dimethyl acrylamide, acrylonitrile, N,N-dimethyl (or diethyl)ethyl methacrylate, 2-methacryloyloxy-ethyl-dimethyl-3-sulfopropyl-ammonium hydroxide, and methoxy PEG methacrylate.

The second monomer usually includes some functional group that may undergo a number of chemical transformations. Examples of the second monomer include hydroxyethyl methacrylate, maleic anhydride, N-hydroxysuccinimide methacrylate ester, methacrylic acid, diacetone acrylamide, glycidyl methacrylate, PEG methacrylate and fumarates.

The repeat unit may be derived from more than two different monomers to provide a polymer having a greater number of points of diversity in terms of binding ability as well as a greater diversity of repeat unit templates on which the anchor site binding ligands are arranged. In the following, for convenience, reference is made to a copolymer of first and second monomers only but additional monomer(s) may be present in the repeat unit.

As required, the polymer may also be modified by incorporation of a spacer between the copolymeric portion and the anchor site binding ligand. The spacer may be used to facilitate attachment of the anchor binding site ligand and further increase spatial distribution between the different anchor binding site ligands. Thus, the spacer will include a chemical group that is reactive towards the copolymer and a separate chemical group that is reactive towards the anchor site ligand in question. Thus, the spacer may be represented by the formula X-Q-Y where X and Y are chemical groups that are reactive towards the copolymer and anchor site ligands respectively.

Typically, X and Y may be the residue of an amino, hydroxyl, thiol, carboxylic acid, anhydride, isocyanate, sulfonyl chloride, sulfonic anhydride, chloroformate, ketone, or aldehyde, provided that X and Y are not reactive with each other or Q. Q is typically a linear or branched divalent organic group. Preferably Q is selected from $C_1$ to $C_{20}$ alkylene, and $C_2$ to $C_{20}$ alkenylene, wherein one or more carbon atoms may be substituted with a heteroatom selected from O, S or N.

In alternative embodiments, the spacer group may have a branched structure whereby multiple functional groups may be attached at the ends of the branches. The spacer group may be attached to the copolymer and then reacted with the anchor binding site ligand. Alternatively, the spacer group may be reacted with the anchor binding site ligand and then this assembly reacted with the copolymer. The spacer may be modified with more than one anchor site binding ligand. The copolymer, spacer groups, functional residues and any other surface components may contribute (positively or negatively) to the total binding strength of the surface to the biomolecule of interest. By tuning any and all of these surface components with respect to one or more anchor site binding ligands, it is possible to preferentially stabilize and maintain a biological molecule in some preferred orientation.

Generally, the polymer coating may be applied to the substrate, or a part thereof, using any of the vast assortment of surface modifications methods known in the art (e.g. dip coating, plasma polymerization, vapor deposition, stamp printing, gamma irradiation, electron beam exposure, thermal and photochemical radiation).

In one embodiment, the polymer coating is graft polymerized from the constituent monomers on the substrate using chemistry well-known in the art. A wide range of polymerization processes present in the art may be utilized. For example, controlled and/or living polymerization techniques of cationic, anionic, radical (such as NMP, ATRP, RAFT, Iniferter), condensation, and metathesis (such as ROMP and ADMET) all may be used. Non-controlled methods of polymerization well known in the art may also be utilized with this invention.

When the polymer includes a functional group and optionally a spacer group, these may be introduced after the copolymer has been graft polymerised onto the surface of the substrate.

Alternatively, the polymer may be applied to the substrate, or a part thereof, as a polymer solution, comprising macromers that will allow tethering by complementary chemistry to the surface of the substrate or encourage entanglement of the polymer in solution with the substrate surface. In the case of a macromer solution, the reactive units of the macromer may either be present at the end groups, or spaced throughout the polymer in a random, block, or gradient fashion.

Preferably, the polymer coating is polymerised from constituent monomers to provide an alternating or block copolymer. The alternating, or substantially alternating character, of the copolymer advantageously increases the non-monotonic nature of the surface coating (i.e. it increases the diversity in possible interaction mechanisms such as hydrophobic, hydrogen-bonding, electrostatic interactions) and hence provides greater diversity of characteristics can be generated by different copolymer formulations. Those skilled in the art will understand the degree to which a large diversity of characteristics can be generated through currently existing monomers and polymerisation techniques. It is preferred that the alternating copolymer has an alternating character defined by greater than 70% of consecutive comonomer residue units being alternate between residues of the first monomer and the second monomer, more preferably greater than 90%. The block nature of the copolymer may also vary in an alternating fashion.

It may also be possible to apply the polymer as a simple coating on the substrate without any covalent binding to the substrate surface. Conventional techniques, such as dip coating, may be used. Crosslinking of the polymer may be required for fixing on the substrate thereby preventing washing off during use. The polymer may be provided on the substrate in ready to use form or it may be functionalised further, for example by introduction of additional functional group(s) as described above.

Alternatively, or in addition, Design of Experiments (DOE) methods well known in the art may be used to control the processes involved in the present invention, including e.g. applying or polymerizing the backbone coating on the substrate, control of chemical reactions involved in further generating the synthon and/or the reactions and interactions occurring in, within or between a population or array of surface coatings on a substrate.

The invention also extends to the use of certain compounds as anchor site binding ligands when suitably provided on a substrate surface. Thus, the invention provides a method of providing a binding surface as described herein, wherein the target molecule is IgG and the anchor site binding ligand is selected from the group consisting of 5-(4-Hydroxymethyl-3-methoxyphenoxy)valeric acid (CAS 213024-57-8), 9-Fluorenylmethoxycarbonyl-L-phenylalanine (CAS 35661-40-6), Glycocholic acid hydrate (CAS 475-31-0) and 2,4-Dinitrophenyl-alpha-aminocaproic acid (CAS 10466-72-5). The invention also provides a method of providing a binding surface as described herein, wherein the target molecule is IgG and the anchor site binding ligand is selected from group consisting of Mycophenolic acid (CAS 24280-93-1), Lavendustin A (CAS 125697-92-9), Pteroic acid (CAS 119-24-4), N10-(trifluoroacetyl)pteroic acid (CAS 37793-53-6), 3-Hydroxy-4-(2-hydroxy-4-sulfo-1-naphthyl azo)naphthalene-2-carboxylic acid (CAS 3737-95-9), N-(4-Nitrobenzoyl)-6-aminocaproic acid, 5-(4-(2-Pyridylsulfamoyl)phenylazo) salicylic acid (CAS 599-79-1), 1,3,4,5-Tetrahydroxycyclohexanecarboxilic acid 3-[3,4-dihydroxycinnamate] (CAS 6001-76-9), Succinylsulfathiazole (CAS 116-43-8), Asp-Ala beta-naphthylamide, 3-carboxyumbelliferyl beta-D-galactopyranoside (CAS 64664-99-9), 4-(N-[2,4-Diamino-6-pteridinylmethyl]-N-methylamino)benzoic acid hemihydrochloride (CAS 19741-14-1), L-Glutamic acid gamma-(7-amido-4-methylcoumarin) (CAS 72669-53-5), His-Ser (CAS 21438-60-8), N-[7-Nitrobenz-2-oxa-1,3-diazol-4-YL]aminohexanoic acid (CAS 88235-25-0), Tyr-Ala (CAS 730-08-5), Nepsilon-Trifluoroacetyl-Lys-Pro (CAS 103300-89-6), N 10-(Trifluoroacetyl)pteroic acid (CAS 37793-53-6), Ala-Trp (CAS 16305-75-2), Ala-His (CAS 3253-17-6), N-(2,4-Dinitrophenyl)-L-tryptophan (CAS 1655-51-2). The invention also relates to binding surfaces and substrates that have been prepared using these methods, i.e. using the various compounds as anchor site binding ligands.

As a general point, it may be possible to use structural analogues of compounds that are identified as potentially useful anchor site binding ligands, provided that such analogues include at least four pharmacophore centres in common with the compound. In this respect the compounds themselves may be used as leads to identify other structurally related and useful compounds.

Where specific compounds are referred to above as being the anchor site binding ligand, it will be appreciated that the compound must be coupled to a substrate prior to use. It is envisaged that this coupling will rely on a functional group present in the compound. This is described above in relation to compounds including a carboxylic acid functionality.

Aspects of the present invention are illustrated in the accompanying non-limiting figures in which:

FIG. 3 is a schematic showing how pharmacophore modelling may be carried out in practice using 4 centers pharmacophore keys;

FIG. 4A is a computer generated representation showing the binding of two anchor site binding ligands to the anchor sites of a protein molecule;

FIG. 4B shows schematically the attachment of two anchor site binding ligands to a surface through a polymeric backbone derived from styrene and maleic anhydride.

Embodiments of the present invention are illustrated in the following non-limiting example.

EXAMPLE

Design of Surface Coatings for Capture and Display of Antibodies

The present invention provides a method of designing and assessing binding surface for a given target molecule and has been applied in this example to the design of surface coatings for capture and display of antibodies. The method involves a series of steps as follows:

(a) Identification within Target Molecule of an Anchor Site which is Remote from the Functional Binding Site Antibodies or immunoglobulins are host proteins produced by B-lymphocytes and plasma cells in response to the presence of a specific antigen (foreign molecule) and are capable of reacting with that antigen. The fine-specificity of antigen recognition by monoclonal antibodies coupled with the relative ease of producing them has resulted in widespread use of monoclonal antibodies in both research and medicine.

IgG antibodies are among one of the five major classes of immunoglobulins that also include IgA, IgD, IgE, and IgM antibodies. Each antibody class is distinguished by certain effector functions and structural features. In some species, the immunoglobulin classes are further differentiated according to subclasses, adding another layer of complexity to antibody structure. In humans, for example, IgG antibodies comprise four IgG subclasses, that is IgG1, IgG2, IgG3, and IgG4. Each subclass corresponds to a different heavy chain isotype.

Figure 1:
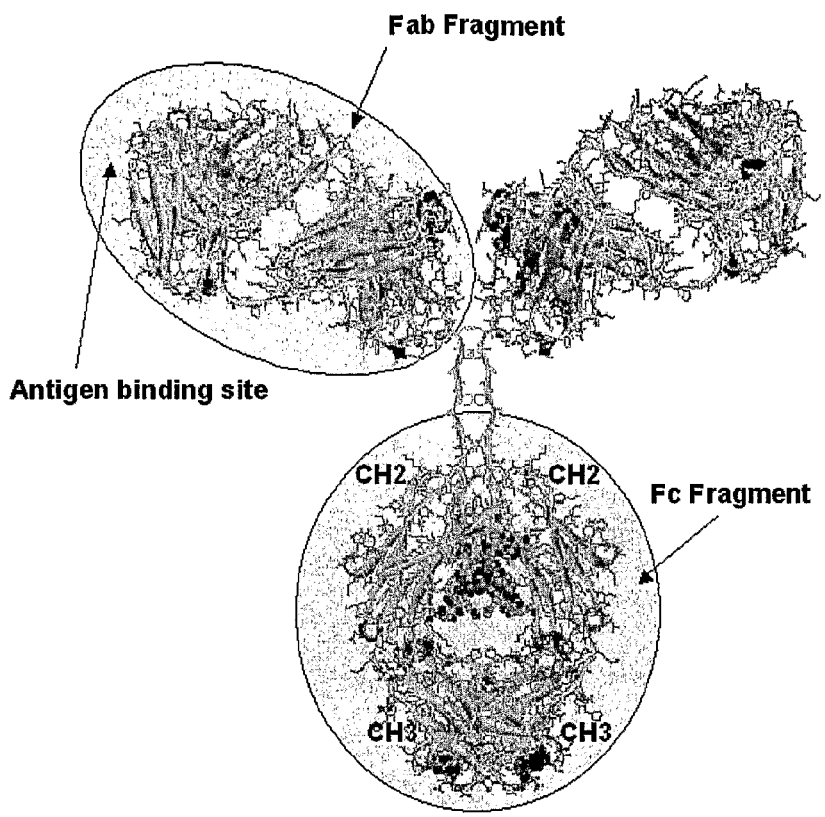
FIG. 1 is a schematic illustrating the structure of an immunoglobulin (IgG)

Antibodies exhibit two fundamental types of structural variation, namely the Fab and the Fc fragments (see FIG. 1 below). Subtle structural differences in their Fab antigen combining sites, or variable regions, account for their unique antigen binding specificities. In the context of the present invention the functional binding site corresponds to the Fab fragment that binds the antigen. Structural differences outside the antigen combining sites, in the so-called constant regions or Fc fragment, correlate with different effector functions mediated by antibodies, such as complement activation or binding to one or more of the antibody Fc receptors expressed on monocytes and granulocytes. The variable and constant regions of antibodies arise from distinct structural domains, such as the $C_{H2}$ and $C_{H3}$ domains for the Fc fragment. If bound to a solid surface through the Fc fragment, both Fab fragments will be oriented correctly for maximal interaction with the antigens. The anchor site (which is remote from the functional binding site) corresponds to the Fc fragment, and more precisely the $C_{H2}$ and $C_{H3}$ domains (see FIG. 1).

It is well known by those skilled in the art that both protein A and protein G bind to the Fc fragment of antibodies. Protein A has different affinities for antibodies from different species, classes and sub-classes. Interestingly, protein G has a different spectrum of binding affinities from protein A.

Protein A has a high affinity for human, pig, rabbit and guinea pig antibodies; a moderate affinity for horse, cow and mouse antibodies; and a low or no affinity for sheep, goat, chicken, hamster and rat antibodies. Protein G has a high affinity for human, horse, cow, pig and rabbit antibodies; a moderate affinity for sheep, goat, hamster, guinea pig, rat and mouse antibodies; and a low affinity for chicken antibodies. When using monoclonal antibodies, protein A has a high affinity for human $IgG_1$, $IgG_2$, $IgG_3$, for mouse $IgG_{2a}$ and $IgG_{2b}$; a moderate or low affinity for mouse $IgG_1$ and $IgG_3$, for rat $IgG_{2c}$; and no affinity for human $IgG_1$, for rat $IgG_1$, $IgG_{2a}$ and $IgG_{2b}$. Protein G has a high affinity for human $IgG_1$, $IgG_2$, $IgG_3$ and $IgG_4$, for mouse $IgG_1$, $IgG_{2a}$, $IgG_{2b}$ and $IgG_3$, for rat $IgG_{2a}$; a moderate or low affinity for rat $IgG_1$, $IgG_{2b}$ and $IgG_{2c}$.

Protein A is a 42,000 dalton protein that is a cell-wall-associated protein of *S. Aureus*. Protein A has five consecutive highly homologous domains that all present an IgG binding activity and has also a region that anchor the protein in the cell wall. The crystal structure of the Fc fragment of human IgG and it's complex with fragment B of protein A was solved to 2.9 Å resolution (J. Deisenhofer, Crystallographic Refinement and Atomic Models of a Human Fc Fragment and its Complex with Fragment B of Protein A from *Staphylococcus aureus* at 2.9 and 2.8 Å Resolution. Biochemistry, 20: 2361-

2370, 1981). The crystal structure is available at the PDB under the code 1FC2 (http://www.rcsb.org/pdb/cgi/explore.cgi?pdbId=1FC2).

Protein G is a 30,000 to 35,000 dalton protein isolated from the cell wall of beta-hemolytic Streptococci. Protein G has three (or 2) highly homologous domains named $C_1$, $C_2$ and $C_3$ (or $B_1$ and $B_2$) that are located at the C-terminal end of the molecule whereas an albumin binding region is present at the N-terminal part. The crystal structure of the Fc fragment of human IgG and it's complex with fragment $C_2$ of protein G was solved to 3.5 Å resolution (Sauer-Eriksson, A. E., Kleywegt, G. J., Uhl, M., Jones, T. A. 1995. Crystal structure of the C2 fragment of streptococcal protein G in complex with the Fc domain of human IgG. Structure 3:265-278.). The crystal structure is available at the PDB under the code 1FCC (http://www.rcsb.org/pdb/cgi/explore.cgi?pdbId=1FCC).

Figure 2:
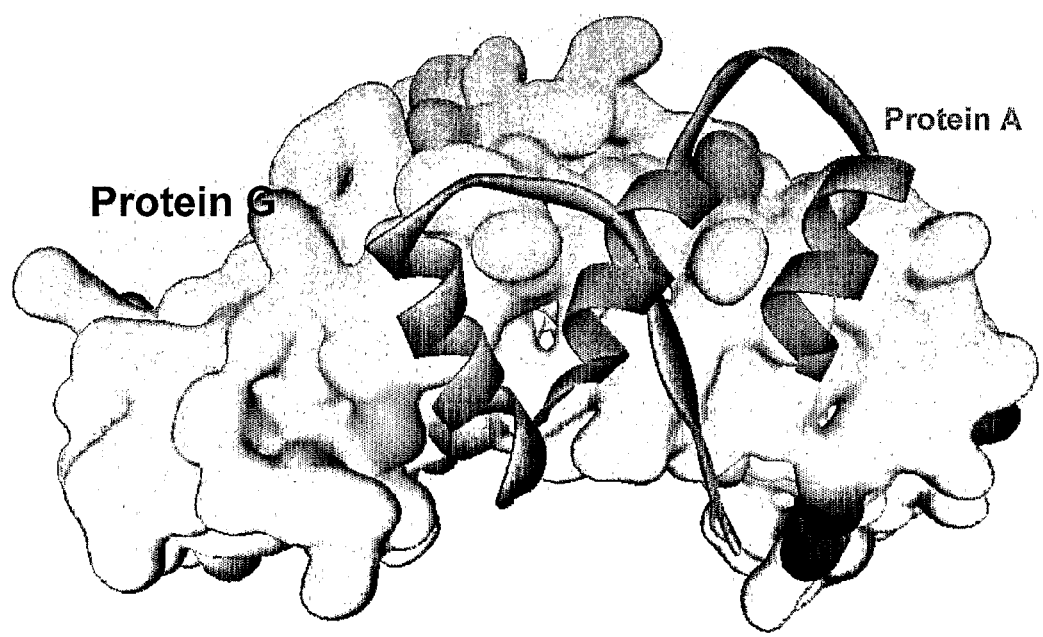
FIG. 2 is a computer generated representation in which crystal structures of human IgG Fc fragment are superposed and where only the interacting regions of the proteins A and G are displayed.

From these crystallographic studies, it has been shown that both protein A and protein G bind to the Fc fragment in slightly different binding modes. The protein G:Fc complex involves mainly charged and polar contacts and is mainly located on the $C_{H3}$ domain, whereas protein A and Fc are held together through non-specific hydrophobic interactions and a few polar interactions and the complex is located at the hinge that connects the $C_{H2}$ and $C_{H3}$ domains. Several residues of the Fc fragment are involved in both the protein G:Fc and the protein A:Fc complex, as shown by the superposition of both crystal structures and where only interacting region of the protein A and G are displayed (see FIG. 2).

Due to their interaction with the Fc fragment, to their different spectrum of IgG binding affinities, to their close but different binding modes and to the availability of crystal structures, both the protein G:Fc and protein A:Fc complexes were ideal to generate pharmacophore models for the targeted anchor sites.

(b) Generation of a Pharmacophore Model for the Anchor Site

The pharmacophore models used in this example consist of the hydrogen bond donor feature (D), the hydrogen bond acceptor feature (A), the positive charge feature (P), the negative charge feature (N) and the aromatic feature (R) arranged in three-dimensional space. When identified, pharmacophoric features are assigned to corresponding centres and stored in the coordinate system of the structure. The A, D, P and N centres are placed on the corresponding atoms using their coordinates. For R centre, a dummy atom is placed at the centre of the aromatic ring.

In order to have the same coordinate system for both models derived from the protein G:Fc and protein A:Fc complexes, the crystal structure of the protein A:Fc complex was overlaid on the crystal structure of the protein G:Fc complex using VMD 1.8 software. The overlay was performed based on the Calpha atoms for the residue that form the binding sites (250-254; 310-315; 380-382; 428-438).

For both models, the binding sites were defined by selecting residues with at least one atom within 5 Å of the binding protein. An hydrogen bond was considered if the distance between the acceptor and donor heavy atoms was less than 4.5 Å. The resulting models are given below.

Model from the Protein G:Fc Complex:

| HETATM | 1 D | PHM | 1 | 19.077 | 8.971 | −4.248 |
|---|---|---|---|---|---|---|
| HETATM | 2 A | PHM | 1 | 14.113 | 4.201 | 1.536 |
| HETATM | 3 A | PHM | 1 | 17.918 | 3.486 | 1.481 |
| HETATM | 4 D | PHM | 1 | 19.523 | 4.191 | 0.055 |

-continued

| HETATM | 5 D | PHM | 1 | 22.973 | 3.731 | −12.398 |
|---|---|---|---|---|---|---|
| HETATM | 6 P | PHM | 1 | 22.973 | 3.731 | −12.398 |
| HETATM | 7 A | PHM | 1 | 17.675 | −3.346 | −14.103 |
| HETATM | 8 D | PHM | 1 | 20.027 | −2.937 | −4.790 |
| HETATM | 9 P | PHM | 1 | 20.027 | −2.937 | −4.790 |
| HETATM | 10 A | PHM | 1 | 18.730 | −4.692 | −8.723 |
| HETATM | 11 N | PHM | 1 | 18.730 | −4.692 | −8.723 |
| HETATM | 12 A | PHM | 1 | 18.943 | −4.570 | −6.637 |
| HETATM | 13 N | PHM | 1 | 18.943 | −4.570 | −6.637 |
| HETATM | 14 A | PHM | 1 | 17.605 | 4.042 | −7.871 |
| HETATM | 15 A | PHM | 1 | 16.447 | 3.281 | −2.678 |
| HETATM | 16 A | PHM | 1 | 15.488 | 4.973 | −0.044 |
| HETATM | 17 A | PHM | 1 | 17.150 | −10.860 | 3.276 |
| HETATM | 18 A | PHM | 1 | 18.498 | −9.659 | 4.599 |
| HETATM | 19 A | PHM | 1 | 19.234 | 0.030 | 5.560 |
| HETATM | 20 A | PHM | 1 | 15.280 | 2.119 | 3.454 |
| HETATM | 21 D | PHM | 1 | 15.899 | −2.550 | 3.774 |
| HETATM | 22 D | PHM | 1 | 16.681 | −2.635 | −0.888 |
| HETATM | 23 D | PHM | 1 | 14.593 | 0.361 | 4.634 |

This Model May be Approximated to Represent the Complex as Follows:

| | | Coordinates | |
|---|---|---|---|
| Feature type | X | Y | Z |
| D | 19.1 | 9.0 | −4.2 |
| A | 14.1 | 4.2 | 1.5 |
| A | 17.9 | 3.5 | 1.5 |
| D | 19.5 | 4.2 | 0.1 |
| D | 23.0 | 3.7 | −12.4 |
| P | 23.0 | 3.7 | −12.4 |
| A | 17.7 | −3.3 | −14.1 |
| D | 20.0 | −2.9 | −4.8 |
| P | 20.0 | −2.9 | −4.8 |
| A | 18.7 | −4.7 | −8.7 |
| N | 18.7 | −4.7 | −8.7 |
| A | 18.9 | −4.6 | −6.6 |
| N | 18.9 | −4.6 | −6.6 |
| A | 17.6 | 4.0 | −7.9 |
| A | 16.4 | 3.3 | −2.7 |
| A | 15.5 | 5.0 | 0.0 |
| A | 17.2 | −10.9 | 3.3 |
| A | 18.5 | −9.7 | 4.6 |
| A | 19.2 | 0.0 | 5.6 |
| A | 15.3 | 2.1 | 3.5 |
| D | 15.9 | −2.6 | 3.8 |
| D | 16.7 | −2.6 | −0.9 |
| D | 14.6 | 0.4 | 4.6 |

Model from the Protein A:Fc Complex:

| HETATM | 1 A | PHM | 2 | 18.604 | −19.135 | 1.282 |
|---|---|---|---|---|---|---|
| HETATM | 2 D | PHM | 2 | 13.943 | −6.457 | −8.546 |
| HETATM | 3 D | PHM | 2 | 18.539 | −4.313 | −6.079 |
| HETATM | 4 R | PHM | 2 | 18.717 | −8.843 | −1.743 |
| HETATM | 5 D | PHM | 2 | 13.824 | −0.683 | 1.203 |
| HETATM | 6 D | PHM | 2 | 22.083 | −2.071 | 4.645 |
| HETATM | 7 R | PHM | 2 | 19.961 | −3.084 | 3.111 |
| HETATM | 8 R | PHM | 2 | 18.000 | 0.350 | −6.650 |
| HETATM | 9 A | PHM | 2 | 14.103 | −2.673 | −8.529 |
| HETATM | 10 A | PHM | 2 | 20.108 | −3.926 | −4.484 |
| HETATM | 11 A | PHM | 2 | 18.231 | −18.189 | 3.308 |
| HETATM | 12 D | PHM | 2 | 18.231 | −18.189 | 3.308 |
| HETATM | 13 N | PHM | 2 | 19.175 | −18.147 | −10.778 |
| HETATM | 14 A | PHM | 2 | 18.748 | −19.432 | −8.668 |
| HETATM | 15 N | PHM | 2 | 18.748 | −19.432 | −8.668 |
| HETATM | 16 A | PHM | 2 | 18.559 | −16.971 | −8.656 |
| HETATM | 17 N | PHM | 2 | 18.559 | −16.971 | −8.656 |

-continued

| | | | | | | |
|---|---|---|---|---|---|---|
| HETATM | 18 A | PHM | 2 | 19.175 | −18.147 | −10.778 |
| HETATM | 19 A | PHM | 2 | 15.931 | −1.237 | −9.617 |
| HETATM | 20 D | PHM | 2 | 18.892 | −3.019 | −10.350 |
| HETATM | 21 A | PHM | 2 | 18.539 | −4.313 | −6.079 |
| HETATM | 22 P | PHM | 2 | 20.264 | −13.684 | 6.915 |
| HETATM | 23 D | PHM | 2 | 20.264 | −13.684 | 6.915 |
| HETATM | 24 P | PHM | 2 | 18.436 | −15.464 | −6.156 |
| HETATM | 25 D | PHM | 2 | 18.436 | −15.464 | −6.156 |
| HETATM | 26 A | PHM | 2 | 16.063 | −4.392 | −1.245 |
| HETATM | 27 A | PHM | 2 | 14.267 | −3.653 | 1.316 |

This Model May be Approximated to Represent the Complex as Follows:

| | Coordinates | | |
|---|---|---|---|
| Feature type | X | Y | Z |
| A | 18.6 | −19.1 | 1.3 |
| D | 13.9 | −6.5 | −8.5 |
| D | 18.5 | −4.3 | −6.1 |
| R | 18.7 | −8.8 | −1.7 |
| D | 13.8 | −0.7 | 1.2 |
| D | 22.1 | −2.1 | 4.6 |
| R | 20.0 | −3.1 | 3.1 |
| R | 18.0 | 0.4 | −6.7 |
| A | 14.1 | −2.7 | −8.5 |
| A | 20.1 | −3.9 | −4.5 |
| A | 18.2 | −18.2 | 3.3 |
| D | 18.2 | −18.2 | 3.3 |
| N | 19.2 | −18.1 | −10.8 |
| A | 18.7 | −19.4 | −8.7 |
| N | 18.7 | −19.4 | −8.7 |
| A | 18.6 | −17.0 | −8.7 |
| N | 18.6 | −17.0 | −8.7 |
| A | 19.2 | −18.1 | −10.8 |
| A | 15.9 | −1.2 | −9.6 |
| D | 18.9 | −3.0 | −10.4 |
| A | 18.5 | −4.3 | −6.1 |
| P | 20.3 | −13.7 | 6.9 |
| D | 20.3 | −13.7 | 6.9 |
| P | 18.4 | −15.5 | −6.2 |
| D | 18.4 | −15.5 | −6.2 |
| A | 16.1 | −4.4 | −1.2 |
| A | 14.3 | −3.7 | 1.3 |

The coordinates of the two models define the relative relationship between the centres and any rotation or translation of the coordinates cannot be interpreted as a different model. Also, proteins are flexible entities and the x-ray determination is not without errors. A tolerance of 2 Å for each centre can be allowed. The pharmacophore models for the protein G:Fc and protein A:Fc complexes, their combination and their use form part of the present invention. The pharmacophore models comprise at least four of the various feature types and coordinates combinations.

Hydrophobic/Lipophilic (H) features were not include in the models for screening but could have been included as follow Lipophilic Centers from the Protein G:Fc Complex:

| | | | | | | |
|---|---|---|---|---|---|---|
| HETATM | 24 H | PHM | 1 | 21.729 | 2.017 | −11.089 |
| HETATM | 25 H | PHM | 1 | 20.033 | −3.038 | −13.663 |
| HETATM | 26 H | PHM | 1 | 18.212 | −1.391 | −4.663 |
| HETATM | 27 H | PHM | 1 | 20.033 | −3.038 | −13.663 |
| HETATM | 28 H | PHM | 1 | 18.212 | −1.391 | −4.663 |

This Model May be Approximated to Represent the Complex as Follows:

| | Coordinates | | |
|---|---|---|---|
| Feature type | X | Y | Z |
| H | 21.7 | 2.0 | −11.1 |
| H | 20.0 | −3.0 | −13.7 |
| H | 18.2 | −1.4 | −4.7 |
| H | 20.0 | −3.0 | −13.7 |
| H | 18.2 | −1.4 | −4.7 |

Lipophilic Centers from the Protein A:Fc Complex:

| | | | | | | |
|---|---|---|---|---|---|---|
| HETATM | 28 H | PHM | 2 | 10.831 | −9.165 | −3.088 |
| HETATM | 29 H | PHM | 2 | 12.765 | −9.826 | −1.570 |
| HETATM | 30 H | PHM | 2 | 20.625 | −11.344 | 3.096 |
| HETATM | 31 H | PHM | 2 | 21.159 | −9.233 | 1.810 |
| HETATM | 32 H | PHM | 2 | 16.414 | −13.254 | −1.454 |
| HETATM | 33 H | PHM | 2 | 17.248 | −12.533 | 1.245 |

This Model May be Approximated to Represent the Complex as Follows:

| | Coordinates | | |
|---|---|---|---|
| Feature type | X | Y | Z |
| H | 10.8 | −9.2 | −3.1 |
| H | 12.8 | −9.8 | −1.6 |
| H | 20.6 | −11.3 | 3.1 |
| H | 21.2 | −9.2 | 1.8 |
| H | 16.4 | −13.3 | −1.5 |
| H | 17.2 | −12.5 | 1.2 |

(c) Use of the Pharmacophore Model to Identify an Anchor Site Binding Ligand

1) Anchor Site Binding Ligand Screening Database 9,289 available mono carboxylic acids were extracted from the ChemFinder ChemACX2000 database and concatenated into an SD file. The CsNum was used as a unique identifier. The SD file was converted into a SMILES file and aromatisation was applied (use of lower case aromatic notation in the SMILES string instead of a Kékule format). Any molecules with a salt, within mixtures, or with atoms other than F, O, N, H, C, Cl, S, Br, P, and I were removed, leading to a dataset of 7,595 compounds.

Since the compounds were extracted from supplier databases, it was assumed that the right stereochemistry at chiral centres and cis/trans double bonds was correctly depicted. Otherwise, the generation of all possible stereoisomers could have been performed. Also, for this example, no attempt was made to take into account the possible tautomeric or ionic forms of a given compound. There is no way to know a priori which tautomer is most likely to bind to the receptor, as the pH at the interface is unknown. It would have been preferable to include all the tautomers as possible structures. Stergen or Tautomer software could be used for that purpose.

In order to avoid excessive computational time in generating the conformers, any molecules with more than 10 rotatable bonds were removed, leading to a final dataset of 6,571 compounds.

2) Pharmacophore Screening Database

Due to the computational time required to determine pharmacophore features and to generate all plausible conformations within a molecule, the pharmacophore screening databases are generated once so that they can be re-screened later in other pharmacophore models.

The approach used here is inspired from the Think methodology. It uses the notion of 4 centre distance keys (see FIG. 3 below). The first 4 letters of the key represent the nature (A, D, N, P or R) of the 4 centres that make the key. The order of the letters is determined by their alphabetical order. When a key is made from centres of the same feature, then the order is determined by a set of rules based on their relative distances to other centres or between themselves. The next 6 digits of the key encode the 6 distances between the 4 centres. The distances d1, d2, d3, d4, d5 and d6 are always defined in the same way. "d1" is the distance between the first and the second centres. "d2" is the distance between the first and the third centres. "d3" is the distance between the first and the fourth centres. "d4" is the distance between the second and the third centres. "d5" is the distance between the second and the fourth centres. "d6" is the distance between the third and the fourth centres. A letter code (0, 1, . . . , 9, a, . . . z) is associated to each distance using a binning scheme. For example, a bin "0" means that the distance between the two centres is less than 3 Å; a bin "4" means that the distance between the two centres is between than 6 and 7 Å. The binning scheme can be changed but this implies rebuilding the pharmacophore screening database.

One key encodes a set of four centres for a given conformation. For a given molecule, all possible combinations of 4 centres need to be generated and all possible conformation need to be considered. The pharmacophore definition of a molecule can be viewed as the logical "OR" of all the keys thus generated.

For conformational sampling, a systematic search was performed using an increment of 120 degrees for a $sp^3$-$sp^3$ bond, 60 degrees for $sp^3$-$sp^2$ bonds and 180 degrees for $sp^2$-$sp^2$ bonds.

A pharmacophore screening database for the 6,571 monocarboxylic acids was generated using a binning scheme of 11 bins with the following limit: <3, <4, <5, <6, <7, <9, <11, <14, <17, <20 and >20. The pharmacophore perception failed for some molecules leading to a final of database of 5690 compounds described by 8,685,484 pharmacophore "screening" keys.

3) Screening of Candidate Anchor Binding Site Ligands Against the Pharmacophore Models Using the same methodology as described for generating the pharmacophore screening keys, pharmacophore "query" keys were generated from the pharmacophore models derived from the protein G:Fc and protein A:Fc complexes. All possible combinations of 4 centres are generated but only one conformation corresponding to the model is used. 6,665 and 12701 unique 4-center pharmacophore query keys were generated from the 23 and 27 centres of the protein G:Fc and protein A:Fc models respectively.

For each candidate molecule of the screening database, a score of 1 is added to the molecule score each time one of its pharmacophore screening key matches a query key. Molecules with at least a score of one can be considered as a hit, but the higher the score, the better the molecule may complement the anchor site. In the present design, 1,385 and 1,099 compounds gave a score greater than one, but only compounds with a score greater that eleven were further considered, leading to the selection of 431 and 258 compounds based on the protein G:Fc and protein A:Fc models respectively.

Compounds selected from the pharmacophore screening were docked onto the rigid anchor site based on each matched key. For each configuration, a conformational analysis is performed to remove conformations where atoms from the ligand collide with atoms from the anchor site. Plausible complexes were scored using the ChemScore function. (M. D. Eldridge, C. W. Murray, T. R. Auton, G. V. Paolinine, and R. P. Mee J. Computer-Aided Molecular Design 11:425-445 (1997).)

A visual inspection of the complexes was performed to check the availability of the carboxylic acid used for coupling to the substrate while keeping the binding characteristics. For the retained configuration, the difference in AM1 intramolecular energies between the bound and the optimised unbound ligand was taken into account. Configurations where the difference was greater than 15 kcal/mol were rejected.

The proprietary, public domain and/or commercial softwares, the scoring function and pharmacophore models that have been used in this example are continually updated and upgraded to refine the quality and the speed of the design.

Table 1 below gives some examples of 20 compounds of interest selected from the protein G:Fc complex hit list. It is expected that some or all of these compounds will provide suitable antibody binding efficacy within the context of the present invention. IgG binding surfaces and substrates comprising one or more of the compounds as anchor site binding ligand therefore fall within the scope of the present invention.

FIG. 4A below display two of these ligands bound to the $C_H3$ domain and FIG. 4B is a schematic representing a monomeric unit of the surface coating with these two ligands.

TABLE 1

| Name | CAS Number | Structure | Free binding energy (kJ/mol) |
|---|---|---|---|
| MYCOPHENOLIC ACID | 24280-93-1 | 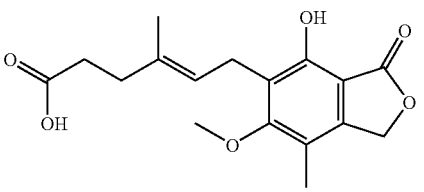 | −31.5 |

TABLE 1-continued

| Name | CAS Number | Structure | Free binding energy (kJ/mol) |
|---|---|---|---|
| LAVENDUSTIN A | 125697-92-9 | 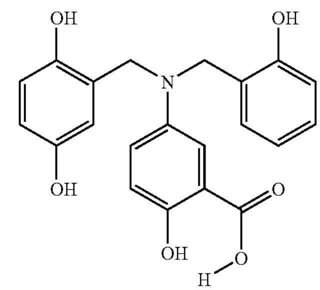 | −51.0 |
| PTEROIC ACID | 119-24-4 | 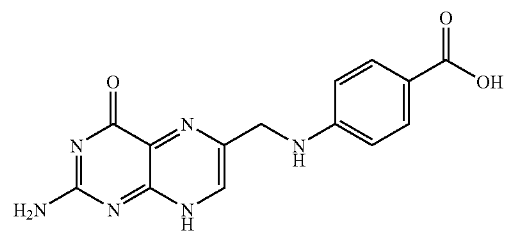 | −41.5 |
| N-10-(TRIFLUOROACETYL)PTEROIC ACID | 37793-53-6 | 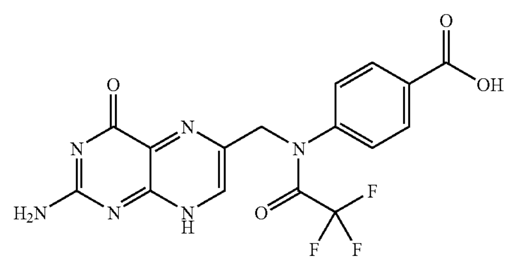 | −39.4 |
| 3-HYDROXY-4-(2-HYDROXY-4-SULFO-1-NAPHTHYLAZO)NAPHTHALENE-2-CARBOXYLIC ACID | 3737-95-9 | 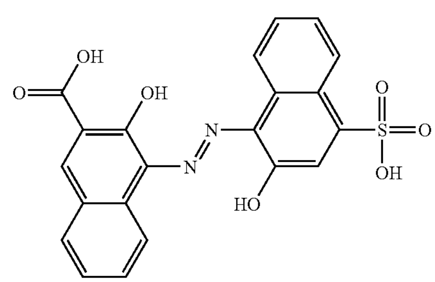 | −45.5 |
| N-(4-NITROBENZOYL)-6-AMINOCAPROIC ACID | | 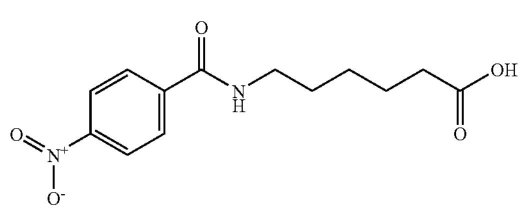 | −40.4 |
| 5-(4-(2-PYRIDYLSULFAMOYL)PHENYLAZO)SALICYLIC ACID | 599-79-1 | 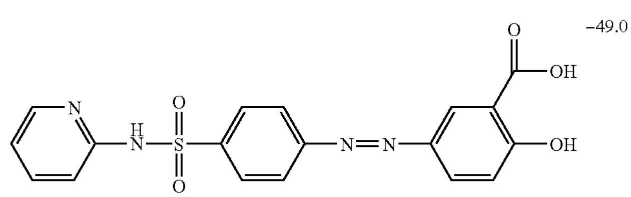 | −49.0 |

TABLE 1-continued

| Name | CAS Number | Structure | Free binding energy (kJ/mol) |
|---|---|---|---|
| 1,3,4,5-TETRAHYDROXYCYCLOHEXANECARBOXYLIC ACID 3-[3,4-DIHYDROXYCINNAMATE | 6001-76-9 | 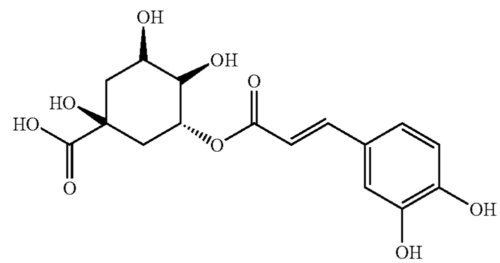 | −44.6 |
| SUCCINYLSULFATHIAZOLE | 116-43-8 | 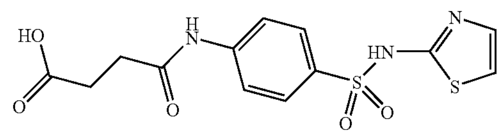 | −39.2 |
| ASP-ALA BETA-NAPHTHYLAMIDE | | 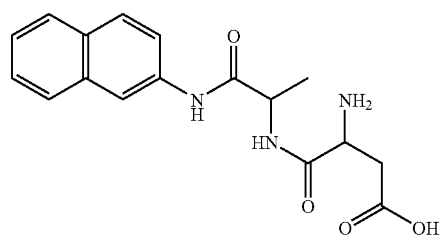 | −36.5 |
| 3-CARBOXYUMBELLIFERYL BETA-D-DALACTOPYRANOSIDE | 64664-99-9 | 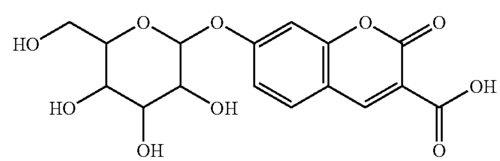 | −50.1 |
| 4-(N-[2,4-DIAMINO-6-PYERIDINYLMETHYL]-N-METHYLAMINO)BENZOIC ACID HEMIHYDROCHLORIDE | 19741-14-1 | 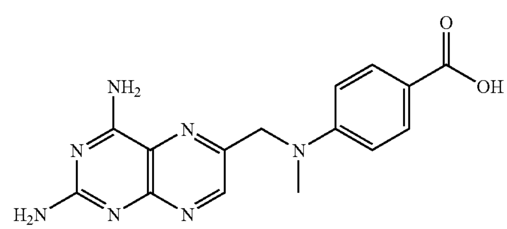 | −35.8 |
| L-GLUTAMIC ACID GAMMA-(7-AMIDO-4-METHYLCOUMARIN) | 72669-53-5 | 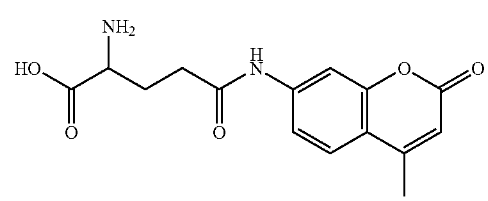 | −34.1 |
| HIS-SER | 21438-60-8 | 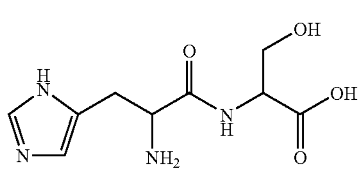 | −22.7 |

TABLE 1-continued

| Name | CAS Number | Structure | Free binding energy (kJ/mol) |
|---|---|---|---|
| N-[7-NITROBENZ-2-OXA-1,3-DIAZOL-4-YL]AMINOHEXANOIC ACID | 88235-25-0 | 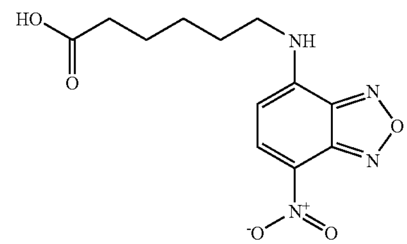 | −31.8 |
| TYR-ALA | 730-08-5 | 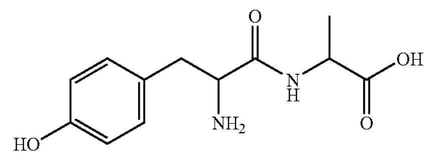 | −42.0 |
| N-EPSILON-TRIFLUOROACETYL-LYS-PRO | 103300-89-6 | 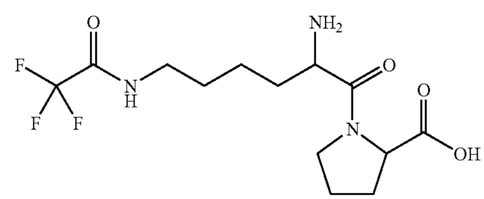 | −30.5 |
| N 10-(TRIFLUOROACETYL)PTEROIC ACID | 37793-53-6 | 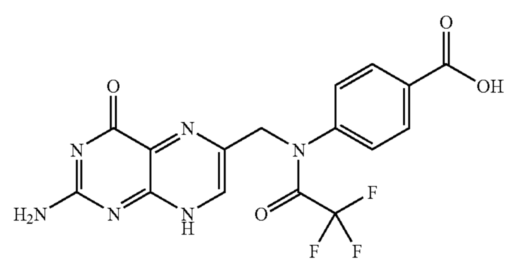 | −26.6 |
| 2,4-DINITROPHENYL-ALPHA-AMINOCAPROIC ACID | 10466-72-5 | 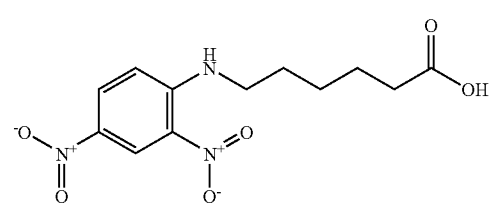 | −30.7 |
| 5-(4-HYDROXYMETHYL-3-METHOXYPHENOXY)VALERIC ACID | 213024-57-8 | | −30.833 | d) Providing the Anchor Site Binding Ligand on a Surface of a Substrate

Surfaces coatings containing sets of 1, 2 or more ligands identified from the virtual screening based on the protein G:Fc and protein A:Fc models may be assembled and tested for their performance in biological assays. More specifically, four single anchor site binding ligands were covalently attached onto poly(ethylenimine) coated Biodyne C membrane and tested in a Thyroid Stimulating Hormone (TSH) sandwich immunoassay. Increased signal in a sandwich assay infers improved capture and display of the primary antibody that is bound to the solid phase. More functional binding sites are available, leading to more TSH antigen being captured and detected by the secondary antibody.

1) Generation of a Polyethylene Coated Biodyne C Membrane.

Biodyne[R] C (0.45μ membrane, Pall Corporation) is one of a family of nylon 6,6 membranes, including Immunodyne ABC, Biodyne A, Biodyne B, Biodyne C amongst others. Biodyne C has a negatively charged surface and its recommended applications are reverse dot blots and dot ELISA. Recommended procedures for its use in ELISA can be obtained from Pall Corporation (http://www.pall.com/OEM_4769.asp). Poly(ethylenimine) of MW of 1800 was obtained from Polysciences, Inc. Diisopropylcarbodiimide (DIC) was obtained from Aldrich and N-Hydroxybenzotriazole (HOBt) was obtained from Auspep.

To amplify the density of ligands on the membrane surface and to couple the correct functional group for coupling pharmacophore acid ligands, Biodyne C membranes were cut into strips (4×1 cm) and immersed in a poly(ethylenimine) (2.16 g, 10 mM), DIC (456 mg, 30 mM) and HOBt (30 mM) solution of DMF and DCM (1:1, 120 mL). The solution was left to stand for 2.5 hrs with occasional shaking. The derivatised membranes were washed with DMF/DCM (2×5 mins) and DCM (3×5 mins), dried and stored in a desiccator.

2) Coupling Carboxylic Acid Ligands to Poly(Ethylenimine) Derivatised Biodyne C.

Ligand Selection: Many of the carboxylic acid ligands identified from the present virtual screening were not available or were too expensive to be acquired as initial building blocks (many of them were part of the Sigma Aldrich Library of Rare Chemicals). Only a total of 15 acids were sourced and of those, 4 were selected for testing on membranes as further described.

TABLE 2

| Membrane number | Compound Name | CAS Number |
|---|---|---|
| M1 | 5-(4-Hydroxymethyl-3-methoxyphenoxy)valeric acid | 213024-57-8 |
| M2 | 9-Fluorenylmethoxycarbonyl-L-phenylalanine | 35661-40-6 |
| M3 | Glycocholic acid hydrate | 475-31-0 |
| M4 | Succinylsulfathiazole | 116-43-8 |

The acids were coupled to the PEI membrane using standard DIC/HOBt activation. In brief, the acids were dissolved with DIC/HOBt in a ratio of 1:2:1 to form a 60 mM solution in DMF. The PEI membranes were left to stand overnight at room temperature.

The membranes were washed 2×5 mins in DMF/DCM (1:1), 3×5 min in DCM and then air dried.

3) Immunoassay: Thyroid Stimulating Hormone (TSH) Sandwich Assay

To validate whether pharmacophore models improved antibody orientation, a TSH sandwich assay was performed on the derivatised membranes. Increased signal in a sandwich assay confirms improved orientation of capture antibody to capture the TSH antigen and consequently, increased binding of the detection antibody. All the steps of the procedure is as below.

a. Solutions Required.
  i. Phosphate buffered saline (PBS): PBS (10×) from Sigma Aldrich (P-7059) was made up to a 10 mM solution with deionised water.
  ii. Blocking solution: 0.5% Hammersten casein (USB Corp), 0.05% Tween-20 (Bio-Rad) in PBS.
b. Application of Capture Antibody: Each strip of derivatised membrane, approximately 4×1 cm, was spotted with Mouse anti-Hu TSH Antibody (OEM Concepts, Clone 057-11003) using a micropipettor: 1 μL of PBS solution containing 87, 43.5 and 8.7 μg per mL is applied with a micropipettor. The membranes were then air dried for 30 mins.
c. Blocking: For four strips of each membrane was blocked with 5 mL PBS containing 0.5% Casein and 0.05% Tween-20 for 60 mins.
d. Antigen: For four strips of each membrane, the blocking solution was replaced by 3 mL of human TSH antigen diluted 1/1000 (2.14 ug/mL) in PBS and incubated for 20 mins at room temperature with agitation.
e. Detection Antibody: For four strips of each membrane, the Antigen solution was replaced by 3 mL of biotinylated mouse anti-human TSH (Medix Biochemica, Clone 5403 biotinylated using EZ-Link-Sulfo-NHS-LC-Biotion from Pierce) diluted 1/5000 (0.2 ug/mL) in PBS. Incubate for 20 mins at room temperature with agitation.
f. Detection: For four strips of each membrane, the detAb was replaced by 3 mL of Streptavidin-HRP diluted 1/5000 (0.2 ug/mL) in PBS. Incubate for 20 mins at room temperature with agitation. Drain and wash 3×5 min (5 mL per wash), with 0.1% Tween-20 in deionised water with agitation. KPL LumiGLO® Chemiluminescent Substrate System was used with a BioRad XRS scanner to image the surface.

4) Data Analysis

Figure 5:
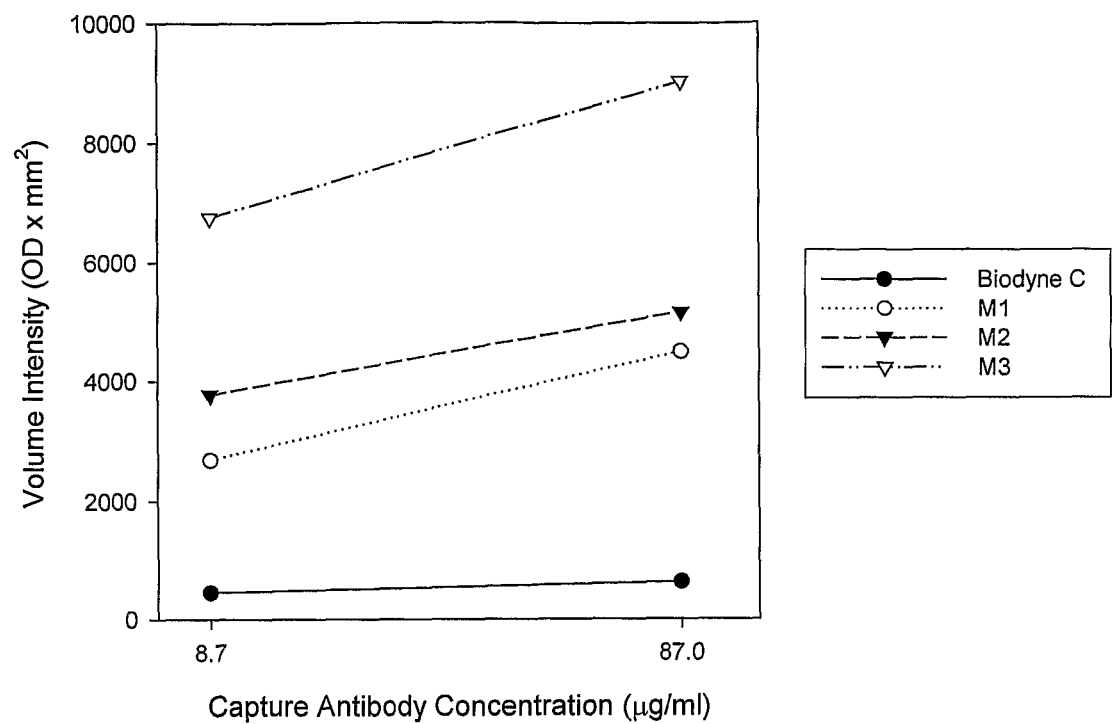
FIG. 5 is a plot of data relating to an example included herein.

Table 3 and the graph included below as FIG. 5 summarize the spot volume intensity (OD×mm2) at 8.7 and 87 ug/ml of capture (primary) IgG concentrations.

Succinylsulfathiazole derivatised membrane M4 displayed high background signal and quantification of the spot volume intensity was not possible. The three other derivatised membranes showed significant increase in signal intensity when compared to the untreated membrane (Biodyne C)

TABLE 3

| | Capture IgG concentrations | | Average signal intensity |
|---|---|---|---|
| Membrane | 8.7 ug/ml | 87 ug/ml | improvement |
| M1 | 2686 | 4485 | 6-fold |
| M2 | 3770 | 5148 | 8-fold |
| M3 | 6750 | 9017 | 14-fold |
| Biodyne C | 459 | 634 | |

The improvement the spot volume intensity compared to the underivatised Biodyne C membrane ranges from 6-fold to 14-fold, Such an increase in signal for a sandwich assay confirms improved orientation of capture antibody to better capture the TSH antigen and consequently, increase the amount of detection antibody being measured.

The reference to any prior art in this specification is not, and should not be taken as, an acknowledgment or any form of suggestion that prior art forms part of the common general knowledge in Australia.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. A method of producing a binding surface for a target molecule having a functional binding site, which method comprises:

(i) identifying within the target molecule an anchor site which is remote from the functional binding site;
(ii) generating a pharmacophore model for the anchor site;
(iii) using the pharmacophore model to identify an anchor site binding ligand; and
(iv) providing the anchor site binding ligand on a surface of a substrate such that the ability of the anchor site binding ligand to bind to the anchor site is preserved.

2. The method according to claim 1, where the anchor site is selected such that when the target molecule is bound to the binding surface, the functional binding site of the target molecule is orientated in such a way as to be available for a subsequent binding interaction with a complementary binding molecule.

3. The method according to claim 2, wherein the target molecule is a protein.

4. The method according to claim 2, wherein the target molecule is an antibody and the complementary binding molecule is an antigen.

5. The method according to claim 4, wherein the Fab region of the antibody corresponds to the functional binding site and the anchor site is located on the Fc region of the antibody.

6. The method according to claim 1, wherein anchor site is identified based on an understanding of the molecular architecture of the target molecule and on the binding characteristics of the functional binding site.

7. The method according to claim 1, wherein the pharmacophore model is a 3-D representation of molecular features defined by reference to at least four feature types.

8. The method according to claim 7, wherein the pharmacophore model is generated by reference to molecular features of the anchor site and/or by reference to molecular features of a set of one or more ligands already known to bind to the anchor site.

9. The method according to claim 7, wherein the anchor site binding ligand matches the pharmacophore model with respect to at least four feature types thereof.

10. The method according to claim 1, further comprising a docking step to ensure binding efficacy of the anchor site binding ligand to an anchor site of the target molecule.

11. The method according to claim 10, wherein the docking step is used to rank anchor site binding ligands according to their binding affinity for an anchor site of the target molecule.

12. The method according to claim 1, wherein multiple anchor site binding ligands are provided on the substrate surface to facilitate binding to anchor sites of the same target molecule.

13. The method according to claim 12, wherein the anchor site binding ligands are included as pendant groups on a polymer backbone that forms or is provided on the substrate surface.

14. The method according to claim 13, wherein the polymer is a copolymer of first and second monomers, wherein the first monomer is selected from styrene (optionally substituted), dimethly, acrylamide, acrylonitrile, N,N-dimethyl (or diethyl)ethyl methacrylate, 2-methacryloyloxy-ethyl-dimethyl-3-sulfopropyl-ammounium hydroxide, and methoxy PEG and the second monomer is selected from hydroxyethyl methacrylate, maleic anhydride, N-hydroxysuccinimide methacrylate ester, methacrylic acid, diacetone acrylamide, glycidyl methacrylate, PEG methacrylate and fumarates.

15. The method according to claim 13, wherein the polymer is modified by incorporation of a spacer between the polymer backbone and the anchor site binding ligand.

16. The method according to claim 1, wherein binding of the target molecule is achieved through interaction of at least one anchor site binding ligand and an anchor site of the target molecule, in combination with non-specific binding interactions between other surface components of the substrate and the target molecule.

17. The method according to claim 1, wherein binding of the anchor site binding ligand to an anchor site of the target molecule may be manipulated by controlling prevailing environmental conditions.

18. The method according to claim 1, wherein the target molecule is IgG and the anchor site binding ligand is selected from the group consisting of 5-(4-Hydroxymethyl-3-methoxyphenoxy)valeric acid (CAS 213024-57-8), 9-Fluorenylmethoxycarbonyl-L-phenylalaine (CAS 35661-40-6), Glycocholic acid hydrate (CAS 475-31-0) and 2,4-Dinitrophenyl-alpha-aminocaproic acid (CAS 10466-72-5).

19. The method according to claim 1, wherein the target molecule is IgG and the anchor site binding ligand is selected from group consisting of Mycophenolic acid (CAS 24280-93-1), Lavendustin A (CAS 125697-92-9), Pteroic acid (CAS 119-24-4), N10-(trifluoroacetyl)pteroic acid (CAS 37793-53-6), 3-Hydroxy-4-(2-hydroxy-4-sulfo-1-naphthyl azo) naphthalene-2-carboxylic acid (CAS 3737-95-9), N-4(Nitrobenzoyl)-6-aminocaproic acid, 5-(4-(2-Pyridylsulfamoyl) phenylazo)salicylic acid (CAS 599-79-1), 1,3,4,5-Tetrahydroxycyclohexanecarboxilic acid 3-[3,4-dihydroxycinnamate] (CAS 6001-76-9), Succinylsulfathiazole (CAS 116-43-8), Asp-Ala beta-naphthylamide, 3-carboxyumbellieferyl beta-D-galactopyranoside (CAS 64664-99-9), 4-(N-[2,4-Diamino-6-pteridinylmethyl]-N-methylamino)benzoic acid hemihydrochloride (CAS 19741-14-1), L-Glutamic acid gamma-(7-amido-4-methylcoumarin) (CAS 72669-53-5), His-Ser (CAS 21438-60-8), N-[7-Nitrobenz-2-oxa-1,3-diazol-4-yl]aminohexanoic acid (CAS 88235-25-0), Tyr-Ala (CAS 730-08-5), N-epsilon-Trifluoracetyl-Lys-Pro (CAS 103300-89-6), N-10-(Trifluoracetyl)pteroic acid (CAS 37793-53-6), Ala-Trp (CAS 16305-75-2), Ala-His (CAS 3253-27-6), and N-(2,4-Dinitrophenyl)-L-tryptophan (CAS 1655-51-2).

20. A binding surface produced in accordance with the method of claim 1,
wherein multiple anchor site binding ligands are provided on the substrate surface to facilitate binding to respective anchor sites of the same target molecule; wherein the target molecule is an antibody and
wherein the anchor site binding ligands are included as pendant groups on a polymer backbone that is formed or is provided on the substrate surface; and
wherein the polymer is a copolymer of first and second monomers, wherein the first monomer is selected from styrene (optionally substituted), dimethyl, acrylamide, acrylonitrile, N,N-dimethyl (or diethyl)ethyl methacrylate, 2-methacryloyloxy-ethyl-dimethyl-3-sulfopropyl-ammounium hydroxide, and methoxy PEG and the second monomer is selected from hydroxyethyl methacrylate, maleic anhydride, N-hydroxysuccinimide methacrylate ester, methacrylic acid, diacetone acrylamide, glycidyl methacrylate, PEG methacrylate and fumarates.

21. A binding surface produced in accordance with the method of claim 1, wherein the target molecule is IgG and the anchor site binding ligand is selected from the group consisting of 5-(4-Hydroxymethyl-3-methoxyphenoxy)valeric acid (CAS 213024-57-8), 9-Fluorenylmethoxycarbonyl-L-phenylalanine (CAS 35661-40-6), Glycocholic acid hydrate (CAS 475-31-0) and 2,4-Dinitrophenyl-alpha-aminocaproic acid (CAS 10466-72-5).

22. A binding surface produced in accordance with the method of claim 1, wherein the target molecule is IgG and the anchor site binding ligand is Mycophenolic acid (CAS 24280-93-1), Lavendustin A (CAS 125697-92-9), Pteroic acid (CAS 119-24-4), N10-(trifluoracetyl)pteroic acid (CAS 37793-53-6), 3-Hydroxy-4-(2-hydroxy-4-sulfo-1-naphthyl azo)naphthalene-2-carboxylic acid (CAS 3737-95-9), N-(4-Nitrobenzoyl)-6-aminocaproic acid, (5-(4-2-Pyridylsulfamoyl)phenylazo)salicylic acid (CAS 599-79-1), 1,3,4,5-Tetrahydroxycyclohexanecarboxilic acid 3-[3,4-dihydroxycinnamate] (CAS 6001-76-9), Succinylsulfathiazole (CAS 116-43-8), Asp-Ala beta-naphtylamide, 3-carboxyumbelliferyl beta-D-galactopyransoide (CAS 64664-99-9), 4-(N-[2,4-Diamino-6-pteridinylmethyl]-N-methylamino)benzoic acid hemihydrochloride (CAS 19741-14-1), L-Glutamic acid gamma-(7-amido-4-methylcoumarin) (CAS 72669-53-5), His-Ser (CAS 21438-60-8), N-[7-Nitrobenz-2-oxa-1,3-diazol-4-yl]aminohexanoic acid (CAS 88235-25-0), Tyr-Ala (CAS 730-08-5), N-epsilon-Trifluoracetyl-Lys-Pro (CAS 103300-89-6), N-10-(Trifluoracetyl)pteroic acid (CAS 37793-53-6), Ala-Trp (CAS 16305-75-2), Ala-His (CAS 3253-17-6), and N-(2,4-Dinitrophenyl)-L-tryptophan (CAS 1655-51-2).

* * * * *